(12) United States Patent
Ma et al.

(10) Patent No.: US 11,106,843 B2
(45) Date of Patent: Aug. 31, 2021

(54) SYSTEMS AND METHODS FOR DETERMINING IN-SITU STRESSES BASED ON ORTHOTROPIC ROCK PHYSICS MODEL

(71) Applicant: SOUTHWEST PETROLEUM UNIVERSITY, Sichuan (CN)

(72) Inventors: Tianshou Ma, Chengdu (CN); Junchuan Gui, Chengdu (CN); Ping Chen, Chengdu (CN); Yang Liu, Chengdu (CN); Jianhong Fu, Chengdu (CN)

(73) Assignee: SOUTHWEST PETROLEUM UNIVERSITY, Chengdu (CN)

( * ) Notice: Subject to any disclaimer, the term of this patent is extended or adjusted under 35 U.S.C. 154(b) by 0 days.

(21) Appl. No.: 17/106,270

(22) Filed: Nov. 30, 2020

(65) Prior Publication Data
US 2021/0173976 A1    Jun. 10, 2021

(30) Foreign Application Priority Data
Dec. 6, 2019 (CN) .......................... 201911239424.2

(51) Int. Cl.
*G06F 30/20* (2020.01)
*G01N 33/24* (2006.01)
*G01V 3/10* (2006.01)
*G06F 113/08* (2020.01)
*G06F 111/10* (2020.01)

(52) U.S. Cl.
CPC ............. *G06F 30/20* (2020.01); *G01N 33/24* (2013.01); *G01V 3/10* (2013.01); *G06F 2111/10* (2020.01); *G06F 2113/08* (2020.01)

(58) Field of Classification Search
CPC ..... G06F 30/20; G06F 2111/10; G01N 33/24; G01V 3/10; G01F 2113/08
See application file for complete search history.

(56) References Cited

U.S. PATENT DOCUMENTS

| 2010/0121623 A1* | 5/2010 | Yogeswaren | ........ G01V 99/005 703/2 |
| 2013/0199787 A1* | 8/2013 | Dale | ....................... E21B 43/30 166/302 |

FOREIGN PATENT DOCUMENTS

| CN | 105317430 A | 2/2016 |
| CN | 105370268 A | 3/2016 |

(Continued)

OTHER PUBLICATIONS

Gui Junchuan et al., The Spatial Distribution of Elastic Parameters of Orthotropic Rocks, Journal of Southwest Petroleum University (Science & Technology Edition), 41(3): 13-28, 2019.

(Continued)

*Primary Examiner* — Regis J Betsch
*Assistant Examiner* — Kaleria Knox
(74) *Attorney, Agent, or Firm* — Metis IP LLC

(57) ABSTRACT

The present disclosure provides systems and methods for determining in-situ stresses based on an orthotropic rock physics model. The method may include obtaining multiple physical parameters of a rock; constructing an orthotropic rock physics model based at least in part on the multiple physical parameters; determining multiple stiffness coefficients based on the orthotropic rock physics model; and determining one or more in-situ stresses of the orthotropic rock based on the multiple stiffness coefficients.

20 Claims, 11 Drawing Sheets

(56) References Cited

FOREIGN PATENT DOCUMENTS

| | | | | |
|---|---|---|---|---|
| CN | 106295119 A | * | 1/2017 | ............. G06F 19/00 |
| CN | 106295119 A | | 1/2017 | |
| CN | 106597531 A | | 4/2017 | |
| CN | 106772673 A | | 5/2017 | |
| CN | 108071389 A | | 5/2018 | |
| CN | 108459346 A | | 8/2018 | |
| CN | 108595769 A | | 9/2018 | |
| CN | 108952700 A | | 12/2018 | |
| CN | 108957544 A | | 12/2018 | |
| CN | 109871507 A | | 6/2019 | |

OTHER PUBLICATIONS

Zeng Qingdong et al., Numerical Study of Hydraulic Fracture Propagation Accounting for Rock Anisotropy, Journal of Petroleum Science and Engineering, 160: 422-432, 2018.
First Office Action in Chinese Application No. 201911239424.2 dated Sep. 14, 2020, 12 pages.
Notification to Grant Patent in Chinese Application No. 201911239424.2 dated Oct. 23, 2020, 6 pages.

* cited by examiner

SYSTEMS AND METHODS FOR DETERMINING IN-SITU STRESSES BASED ON ORTHOTROPIC ROCK PHYSICS MODEL

CROSS-REFERENCE TO RELATED APPLICATIONS

This application claims priority of Chinese Patent Application No. 201911239424.2, filed on Dec. 6, 2019, the contents of which are hereby incorporated by reference in its entirety.

TECHNICAL FIELD

The disclosure generally relates to petroleum reservoir management, and more particularly, relates to systems and methods for determining geomechanical based on orthotropic rock physics model.

BACKGROUND

In-situ stress is an important parameter in oil-gas exploration and development. For example, problems such as wellbore stability, casing deformation and damage, etc., are closely related to in-situ stress. Generally, the in-situ stress can be characterized by three parameters including vertical in-situ stress, a maximum horizontal in-situ stress, and a minimum horizontal in-situ stress. Moreover, since the complex geomechanical environment of rock (e.g., shale) and rock bedding and fissures are very developed, the rock usually comprehensively shows significant orthotropic characteristics. Therefore, it is desirable to provide systems and methods for determining the in-situ stress to improve the detection efficiency and accuracy in in-situ stress determination of an orthotropic rock.

SUMMARY

According to an aspect of the present disclosure, a method is provided. The method may be implemented on a computing device including at least one processor and at least one storage medium, and a communication platform connected to a network. The method may include determining multiple physical parameters of an orthotropic rock by well logging, mud logging, and indoor testing, the multiple physical parameters including compositions of minerals, a content of each of the minerals, compositions of formation fluids, a content of each of the formation fluids, a porosity, and a saturation; constructing an orthotropic rock physics model; determining, based on the orthotropic rock physics model, stiffness coefficients; determining, based on the following relationship formulas between stiffness coefficient and elastic parameter, multiple dynamic elastic parameters of the orthotropic rock, $$\begin{cases} E_1 = \Delta/(c_{23}^2 - c_{22}c_{33}) \\ E_2 = \Delta/(c_{13}^2 - c_{11}c_{33}) \\ E_3 = \Delta/(c_{12}^2 - c_{11}c_{22}) \end{cases}$$

$$\Delta = c_{33}c_{12}^2 + c_{22}c_{13}^2 + c_{11}c_{23}^2 - c_{11}c_{22}c_{33} - 2c_{12}c_{13}c_{23}$$

$$\begin{cases} v_{12} = (c_{13}c_{23} - c_{12}c_{33})/(c_{23}^2 - c_{22}c_{33}) \\ v_{13} = (c_{12}c_{23} - c_{13}c_{22})/(c_{23}^2 - c_{22}c_{33}) \\ v_{21} = (c_{13}c_{23} - c_{12}c_{33})/(c_{13}^2 - c_{11}c_{33}) \\ v_{23} = (c_{12}c_{13} - c_{11}c_{23})/(c_{13}^2 - c_{11}c_{33}) \\ v_{31} = (c_{12}c_{23} - c_{13}c_{22})/(c_{12}^2 - c_{11}c_{22}) \\ v_{32} = (c_{12}c_{13} - c_{11}c_{23})/(c_{12}^2 - c_{11}c_{22}) \end{cases}$$

$$\begin{cases} E_2 v_{12} = E_1 v_{21} \\ E_3 v_{13} = E_1 v_{31} \\ E_2 v_{32} = E_3 v_{23} \end{cases}$$

$$\begin{cases} \mu_{23} = c_{44} \\ \mu_{13} = c_{55} \\ \mu_{12} = c_{66} \end{cases}$$

where $c_{11}$, $c_{12}$, $c_{13}$, $c_{22}$, $c_{23}$, $c_{33}$, $c_{44}$, $c_{55}$, and $c_{66}$ denote the stiffness coefficients of the orthotropic rock, GPa; $E_1$ denotes a Young's modulus along a direction of a maximum horizontal in-situ stress, GPa; $E_2$ denotes a Young's modulus along a direction of a minimum horizontal in-situ stress, GPa; $E_3$ denotes a Young's modulus along a direction of a vertical in-situ stress, GPa; $v_{12}$ denotes a Poisson's ratio along the direction of the minimum horizontal in-situ stress and perpendicular to the direction of the maximum horizontal in-situ stress; $v_{13}$ denotes a Poisson's ratio along the direction of the vertical in-situ stress and perpendicular to the direction of the maximum horizontal in-situ stress; $v_{21}$ denotes a Poisson's ratio along the direction of the maximum horizontal in-situ stress and perpendicular to the direction of the minimum horizontal in-situ stress; $v_{23}$ a Poisson's ratio along the direction of the vertical in-situ stress and perpendicular to the direction of the minimum horizontal in-situ stress; $v_{31}$ a Poisson's ratio along the direction of the maximum horizontal in-situ stress and perpendicular to the direction of the vertical in-situ stress; and $v_{32}$ denotes a Poisson's ratio along the direction of the minimum horizontal in-situ stress and perpendicular to the direction of the vertical in-situ stress; determining, based on the multiple dynamic elastic parameters of the orthotropic rock, multiple static elastic parameters of the orthotropic rock according to relationships between the multiple dynamic elastic parameters and the multiple static elastic parameters; determining anisotropy Biot coefficients of the orthotropic rock physics model according to the following formulas:

$$\begin{cases} \alpha_{11} = 1 - \dfrac{c_{11}^{dry} + c_{12}^{dry} + c_{13}^{dry}}{c_{11}^m + c_{12}^m - c_{13}^m} \\ \alpha_{22} = 1 - \dfrac{c_{12}^{dry} + c_{22}^{dry} + c_{23}^{dry}}{c_{11}^m + c_{22}^m + c_{23}^m} \\ \alpha_{33} = 1 - \dfrac{c_{13}^{dry} + c_{23}^{dry} + c_{33}^{dry}}{c_{13}^m + c_{23}^m + c_{33}^m} \end{cases}$$

where $c_{11}^{dry}$, $c_{12}^{dry}$, $c_{13}^{dry}$, $c_{22}^{dry}$, $c_{23}^{dry}$, and $c_{33}^{dry}$ denote stiffness coefficients of a dry orthotropic (ORT) rock, GPa; $c_{11}^m$, $c_{12}^m$, $c_{13}^m$, $c_{22}^m$, $c_{23}^m$, and $c_{33}^m$ denote stiffness coefficients of a dry vertical transverse isotropy (VTI) rock, GPa; and $\alpha_{11}$, $\alpha_{22}$, and $\alpha_{33}$ denote the anisotropy Biot coefficients; determining a formation pore pressure based on longitudinal wave time differences according to an Eaton method described as the following formula:

$$P_p = \sigma_v - (\sigma_v - p_w)(AC_n/AC)^c$$

where $\sigma_v$ denotes the vertical in-situ stress, MPa; $p_w$ denotes a formation hydrostatic column pressure, MPa; $AC_n$ denotes a longitudinal wave time difference of trend line at normal pressure, μs/ft; AC denotes an actual longitudinal wave time difference, μs/ft; and $P_p$ denotes the formation pore pressure, MPa; and determining the maximum horizontal in-situ stress and the minimum horizontal in-situ stress of the orthotropic rock according to the following formulas:

$$\begin{cases} \sigma_H = \frac{v_{13} + v_{12}v_{23}}{1 - v_{12}v_{21}}(\sigma_v - \alpha_{33}P_p) + \alpha_{11}P_p + \frac{E_1}{1 - v_{12}v_{21}}\varepsilon H + \frac{E_1 v_{21}}{1 - v_{12}v_{21}}\varepsilon_h \\ \sigma_h = \frac{v_{23} + v_{13}v_{21}}{1 - v_{12}v_{21}}(\sigma_v - \alpha_{33}P_p) + \alpha_{22}P_p + \frac{E_2}{1 - v_{12}v_{21}}\varepsilon_h + \frac{E_1 v_{21}}{1 - v_{12}v_{21}}\varepsilon_H \end{cases}$$

where $\sigma_H$ denotes the maximum horizontal in-situ stress, MPa; $\sigma_h$ denotes the minimum horizontal in-situ stress, MPa; $\varepsilon_H$ denotes a maximum horizontal strain corresponding to the direction of the maximum horizontal in-situ stress; and $\varepsilon_h$ denotes a minimum horizontal strain corresponding to the direction of the minimum horizontal in-situ stress.

In some embodiments, the constructing an orthotropic rock physics model may include determining an equivalent elastic modulus of matrix minerals using Hashin-Shtrikman bounds; constructing a dry matrix rock by adding inorganic pores to the matrix minerals using an isotropic self-consistent approximation (SCA) model and an isotropic differential effective medium (DEM) model to establish a dry matrix rock physics model and determine an equivalent elastic modulus of the dry matrix rock; determining an equivalent elastic stiffness tensor of organic minerals using an anisotropic SCA model and an anisotropic DEM model; determining an equivalent elastic stiffness tensor of an oriented organic rock based on a confidence level (CL) coefficient and the Bond transform normal distribution, wherein the CL coefficient describes a layered distribution of the organic minerals; constructing a dry organic rock by adding organic pores to the oriented organic rock based on the anisotropic DEM model to establish a dry organic rock physics model and determine an equivalent elastic stiffness tensor of the dry organic rock; constructing a dry vertical transverse isotropy (VTI) rock including pores by adding the dry matrix rock to the dry organic rock based on the anisotropic DEM model to establish a dry VTI rock physics model and determine an elastic tensor of the dry VTI rock; constructing a dry orthotropic (ORT) rock by adding vertically distributed fractures to the dry VTI rock based on an anisotropy Schoenberg linear sliding model to establish a dry ORT rock physics model; determining and converting a bulk modulus of gas-water mixture in the pores into a stiffness tensor based on a Wood formula according to a gas saturation and a water saturation; and combining with orthotropic nature of the dry ORT rock, constructing a saturated fluid ORT rock by adding the formation fluids to the dry ORT rock based on a Brown-Korringa model to establish the orthotropic rock physics model.

In some embodiments, the determining an equivalent elastic modulus of matrix minerals using Hashin-Shtrikman bounds may include determining a maximum bulk modulus, a minimum of bulk modulus, a maximum shear modulus, and a minimum shear modulus of the matrix minerals using the Hashin-Shtrikman bounds; designating an average of the maximum bulk modulus and the minimum bulk modulus as the bulk modulus of the matrix minerals; and designating an average of the maximum shear modulus and the minimum shear modulus as the shear modulus of the matrix minerals.

In some embodiments, the Hashin-Shtrikman bounds may be as the following formula:

$$\begin{cases} K^{HS+} = \Lambda(\mu_{max}), K^{HS-} = \Lambda(\mu_{min}) \\ \mu^{HS+} = \Gamma(\zeta(K_{max}, \mu_{max})), \mu^{HS-} = \Gamma(\zeta(K_{min}, \mu_{min})) \end{cases}$$

where $K^{HS+}$ denotes the maximum bulk modulus, GPa; $K^{HS-}$ denotes the minimum bulk modulus, GPa; $\mu^{HS+}$ denotes the maximum shear modulus, GPa; and $\mu^{HS-}$ denotes the minimum shear modulus, GPa.

In some embodiments, the isotropic SCA model may be as the following formula:

$$\begin{cases} \sum_{i=1}^{N} v_i(K_i - K_{SCA}^+)P^{+i} = 0 \\ \sum_{i=1}^{N} v_i(\mu_i - \mu_{SCA}^+)Q^{+i} = 0 \end{cases}$$

where $v_i$ denotes a volume fraction of the i-th material; $P^{+i}$ denotes a first geometric factor of the i-th material; $Q^{+i}$ denotes a second geometric factor of the i-th material; $K_{SCA}^+$ denotes an equivalent bulk modulus, GPa; and $\mu_{SCA}^+$ denotes an equivalent shear modulus, GPa; and the isotropic DEM model may be as the following formula:

$$\begin{cases} (1-v)\frac{d}{dv}[K^+(v)] = (K_2 - K^+)P^{(+2)}(v) \\ (1-v)\frac{d}{dv}[\mu^+(v)] = (\mu_2 - \mu^+)Q^{(+2)}(v) \end{cases}$$

where $K_1$ denotes a bulk modulus of a background medium, GPa; $\mu_1$ denotes a shear modulus of the background medium, GPa; $K_2$ denotes a bulk modulus of an inclusion, GPa; $\mu_2$ denotes a shear modulus of the inclusion, GPa; and $v$ denotes a volume fraction of the inclusion.

In some embodiments, the anisotropic SCA model may be as the following formula:

$$\tilde{C}_{ijkl}^{SCA} = \sum_{n=i}^{N} v_n \tilde{C}_{ijkl}^n (\tilde{I}_{ijkl} + \tilde{G}_{ijkl}^n (\tilde{C}_{ijkl}^n - \tilde{C}_{ijkl}^{SCA}))^{-1}$$

$$\left\{ \sum_{p=i}^{N} v_p (\tilde{I}_{ijkl} + \tilde{G}_{ijkl}^p (\tilde{C}_{ijkl}^p - \tilde{C}_{ijkl}^{SCA}))^{-1} \right\}^{-1}$$

where $\tilde{C}_{ijkl}^{SCA}$ denotes an equivalent stiffness tensor of the anisotropic SCA model, GPa; $\tilde{G}_{ijkl}^n$ denotes an Eshelby stiffness tensor of the n-th material, GPa; $\tilde{I}_{ijkl}$ denotes a fourth order unit stiffness tensor; $\tilde{C}_{ijkl}^n$ denotes a stiffness tensor of the n-th material, GPa; and $v_n$ denotes a volume fraction of the n-th material; and the anisotropic DEM model may be as the following formula:

$$\frac{d}{dv}\left(\tilde{C}_{ijkl}^{DEM}(v)\right) = \frac{1}{(1-v)}\left(\tilde{C}_{ijkl}^{I} - \tilde{C}_{ijkl}^{DEM}(v)\right)\left[\tilde{I}_{ijkl} + \tilde{G}_{ijkl}^{I}\left(\tilde{C}_{ijkl}^{P} - \tilde{C}_{ijkl}^{DEM}(v)\right)\right]^{-1}$$

where $\tilde{C}_{ijkl}^{DEM}$ denotes a stiffness tensor of the background medium, GPa; $\tilde{C}_{ijkl}^{I}$ denotes a stiffness tensor of the inclusion, GPa; $\tilde{G}_{ijkl}^{I}$ denotes an Eshelby stiffness tensor of the inclusion; $\tilde{I}_{ijkl}$ denotes the fourth order unit stiffness tensor; and v denotes a volume fraction of a material being added, decimal.

In some embodiments, the anisotropy Schoenberg linear sliding model may be as the following formula:

$$C = \begin{bmatrix} c_{11b} - \frac{\Delta_N c_{12b}^2}{c_{11b}} & c_{12b}(1-\Delta_N) & c_{13b}\left(1 - \frac{\Delta_N c_{12b}}{c_{11b}}\right) & 0 & 0 & 0 \\ c_{12b}(1-\Delta_N) & c_{11b}(1-\Delta_N) & c_{13b}(1-\Delta_N) & 0 & 0 & 0 \\ c_{13b}\left(1 - \frac{\Delta_N c_{12b}}{c_{11b}}\right) & c_{13b}(1-\Delta_N) & c_{33b}\left(1 - \frac{\Delta_N c_{13b}^2}{c_{11b}}\right) & 0 & 0 & 0 \\ 0 & 0 & 0 & c_{44b} & 0 & 0 \\ 0 & 0 & 0 & 0 & c_{44b}(1-\Delta_V) & 0 \\ 0 & 0 & 0 & 0 & 0 & c_{66b}(1-\Delta_N) \end{bmatrix}$$

where C denotes a stiffness matrix of the dry ORT rock after adding the vertically distributed fractures, GPa; $c_{11b}$, $c_{12b}$, $c_{13b}$, $c_{33b}$, $c_{4b}$, and $c_{66b}$ denote stiffness coefficients of the dry VTI rock without the vertically distributed fractures, GPa; and $\Delta_N$, $\Delta_V$, and $\Delta_H$ denote weak degrees of characteristics of the vertically distributed fractures.

In some embodiments, the Wood formula may be as the following formula:

$$\begin{cases} K_f = \frac{K_g K_w}{S_g K_w + (1-S_g)_{K_g}} \\ \mu_f = 0 \end{cases}$$

where $K_g$ denotes a bulk modulus of gas, GPa; $K_w$ denotes a bulk modulus of water, GPa; $K_f$ denotes an equivalent bulk modulus of the formation fluids, GPa; $S_g$ denotes a gas saturation; and $\mu_f$ denotes an equivalent shear modulus of the formation fluids, GPa; and the Brown-Korringa model may be as the following formula:

$$S_{ijkl}^{sat} = S_{ijkl}^{dry} - \frac{\left(S_{ijmm}^{dry} - S_{ijmm}^{gr}\right)\left(S_{nnkl}^{dry} - S_{nnkl}^{gr}\right)}{\left(S_{aabb}^{dry} - S_{aabb}^{gr}\right) + \phi(\beta_{fl} - \beta_{gr})}$$

where $S_{ijkl}^{sat}$ denotes a flexibility tensor of the saturated fluid ORT rock, GPa$^{-1}$; $S_{ijkl}^{dry}$ denotes a flexibility tensor of the day ORT rock, GPa$^{-1}$; $S_{ijmm}^{gr}$ denotes a flexibility tensor of the dry VTI rock, GPa$^{-1}$; $\beta_{fl}$ denotes a compressibility factor of the formation fluids, GPa$^{-1}$; $\beta_{gr}$ denotes a compressibility factor of the minerals, GPa$^{-1}$; and Ø denotes the porosity.

In some embodiments, the determining each of the relationships between the multiple dynamic elastic parameters and the multiple static elastic parameters may include determining a dynamic elastic parameter of a core of the orthotropic rock based on one or more wave speeds of the core; determining a static elastic parameter of the core by performing a rock triaxial compression experiment on the core of the orthotropic rock; and determining the relationship between the dynamic elastic parameter and the static elastic parameter.

According to another aspect of the present disclosure, a system is provided. The system may include at least one storage device storing executable instructions, and at least one processor in communication with the at least one storage device. When executing the executable instructions, the at least one processor may cause the system to perform one or more of the following operations. The system may determine multiple physical parameters of an orthotropic rock by well logging, mud logging, and indoor testing, the multiple physical parameters including compositions of minerals, a content of each of the minerals, compositions of formation fluids, a content of each of the formation fluids, a porosity, and a saturation. The system may construct an orthotropic rock physics model. The system may determine, based on the orthotropic rock physics model, stiffness coefficients. The system may determine, based on the following relationship formulas between stiffness coefficient and elastic parameter, multiple dynamic elastic parameters of the orthotropic rock, $$\begin{cases} E_1 = \Delta/(c_{23}^2 - c_{22}c_{33}) \\ E_2 = \Delta/(c_{13}^2 - c_{11}c_{33}) \\ E_3 = \Delta/(c_{12}^2 - c_{11}c_{22}) \end{cases}$$

$$\Delta = c_{33}c_{12}^2 + c_{22}c_{13}^2 + c_{11}c_{23}^2 - c_{11}c_{22}c_{33} - 2c_{12}c_{13}c_{23}$$

$$\begin{cases} v_{12} = (c_{13}c_{23} - c_{12}c_{33})/(c_{23}^2 - c_{22}c_{33}) \\ v_{13} = (c_{12}c_{23} - c_{13}c_{22})/(c_{23}^2 - c_{22}c_{33}) \\ v_{21} = (c_{13}c_{23} - c_{12}c_{33})/(c_{13}^2 - c_{11}c_{33}) \\ v_{23} = (c_{12}c_{13} - c_{11}c_{23})/(c_{13}^2 - c_{11}c_{33}) \\ v_{31} = (c_{12}c_{23} - c_{13}c_{22})/(c_{12}^2 - c_{11}c_{22}) \\ v_{32} = (c_{12}c_{13} - c_{11}c_{23})/(c_{12}^2 - c_{11}c_{22}) \end{cases}$$

$$\begin{cases} E_2 v_{12} = E_1 v_{21} \\ E_3 v_{13} = E_1 v_{31} \\ E_2 v_{32} = E_3 v_{23} \end{cases}$$

$$\begin{cases} \mu_{23} = c_{44} \\ \mu_{13} = c_{55} \\ \mu_{12} = c_{66} \end{cases}$$

where $c_{11}$, $c_{12}$, $c_{13}$, $c_{22}$, $c_{23}$, $c_{33}$, $c_{44}$, $c_{55}$, and $c_{66}$ denote the stiffness coefficients of the orthotropic rock, GPa; $E_1$ denotes a Young's modulus along a direction of a maximum horizontal in-situ stress, GPa; $E_2$ denotes a Young's modulus along a direction of a minimum horizontal in-situ stress, GPa; $E_3$ denotes a Young's modulus along a direction of a vertical in-situ stress, GPa; $v_{12}$ denotes a Poisson's ratio along the direction of the minimum horizontal in-situ stress and perpendicular to the direction of the maximum horizontal in-situ stress; $v_{13}$ denotes a Poisson's ratio along the direction of the vertical in-situ stress and perpendicular to the direction of the maximum horizontal in-situ stress; $v_{21}$ denotes a Poisson's ratio along the direction of the maximum horizontal in-situ stress and perpendicular to the direction of the minimum horizontal in-situ stress; $v_{23}$ a Poisson's ratio along the direction of the vertical in-situ stress and perpendicular to the direction of the minimum horizontal in-situ stress; $v_{31}$ a Poisson's ratio along the direction of the maximum horizontal in-situ stress and perpendicular to the direction of the vertical in-situ stress; and $v_{32}$ denotes a Poisson's ratio along the direction of the minimum horizontal in-situ stress and perpendicular to the direction of the vertical in-situ stress. The system may determine, based on the multiple dynamic elastic parameters of the orthotropic rock, multiple static elastic parameters of the orthotropic rock according to relationships between the multiple dynamic elastic parameters and the multiple static elastic parameters. The system may determine anisotropy Biot coefficients of the orthotropic rock physics model according to the following formulas:

$$\begin{cases} \alpha_{11} = 1 - \dfrac{c_{11}^{dry} + c_{12}^{dry} + c_{13}^{dry}}{c_{11}^{m} + c_{12}^{m} + c_{13}^{m}} \\ \alpha_{22} = 1 - \dfrac{c_{12}^{dry} + c_{22}^{dry} + c_{23}^{dry}}{c_{11}^{m} + c_{22}^{m} + c_{23}^{m}} \\ \alpha_{33} = 1 - \dfrac{c_{13}^{dry} + c_{23}^{dry} + c_{33}^{dry}}{c_{13}^{m} + c_{23}^{m} + c_{33}^{m}} \end{cases}$$

where $c_{11}^{dry}$, $c_{12}^{dry}$, $c_{13}^{dry}$, $c_{22}^{dry}$, $c_{23}^{dry}$, and $c_{33}^{dry}$ denote stiffness coefficients of a dry orthotropic (ORT) rock, GPa; $c_{11}^{m}$, $c_{12}^{m}$, $c_{13}^{m}$, $c_{22}^{m}$, $c_{23}^{m}$, and $c_{33}^{m}$ denote stiffness coefficients of a dry vertical transverse isotropy (VTI) rock, GPa; and $\alpha_1$, $\alpha_{22}$, and $\alpha_{33}$ denote the anisotropy Biot coefficients. The system may determine a formation pore pressure based on longitudinal wave time differences according to an Eaton method described as the following formula:

$$P_p = \sigma_v - (\sigma_v - p_w)(AC_n/AC)^c$$

where $\sigma_v$ denotes the vertical in-situ stress, MPa; $p_w$ denotes a formation hydrostatic column pressure, MPa; $AC_n$ denotes a longitudinal wave time difference of trend line at normal pressure, μs/ft; AC denotes an actual longitudinal wave time difference, μs/ft; and $P_p$ denotes the formation pore pressure, MPa. The system may determine the maximum horizontal in-situ stress and the minimum horizontal in-situ stress of the orthotropic rock according to the following formulas:

$$\begin{cases} \sigma_H = \dfrac{v_{13} + v_{12}v_{23}}{1 - v_{12}v_{21}}(\sigma_v - \alpha_{33}P_p) + \alpha_{11}P_p + \dfrac{E_1}{1-v_{12}v_{21}}\varepsilon_H + \dfrac{E_1 v_{21}}{1-v_{12}v_{21}}\varepsilon_h \\ \sigma_h = \dfrac{v_{23} + v_{13}v_{21}}{1 - v_{12}v_{21}}(\sigma_v - \alpha_{33}P_p) + \alpha_{22}P_p + \dfrac{E_2}{1-v_{12}v_{21}}\varepsilon_h + \dfrac{E_1 v_{21}}{1-v_{12}v_{21}}\varepsilon_H \end{cases}$$

where $\sigma_H$ denotes the maximum horizontal in-situ stress, MPa; $\sigma_h$ denotes the minimum horizontal in-situ stress, MPa; $\varepsilon_H$ denotes a maximum horizontal strain corresponding to the direction of the maximum horizontal in-situ stress; and $\varepsilon_h$ denotes a minimum horizontal strain corresponding to the direction of the minimum horizontal in-situ stress.

According to yet another aspect of the present disclosure, a non-transitory computer readable medium storing at least one set of instructions is provided. When executed by at least one processor, the at least one set of instructions may direct the at least one processor to perform a method. The method may include determining multiple physical parameters of an orthotropic rock by well logging, mud logging, and indoor testing, the multiple physical parameters including compositions of minerals, a content of each of the minerals, compositions of formation fluids, a content of each of the formation fluids, a porosity, and a saturation; constructing an orthotropic rock physics model; determining, based on the orthotropic rock physics model, stiffness coefficients; determining, based on the following relationship formulas between stiffness coefficient and elastic parameter, multiple dynamic elastic parameters of the orthotropic rock, $$\begin{cases} E_1 = \Delta/(c_{23}^2 - c_{22}c_{33}) \\ E_2 = \Delta/(c_{13}^2 - c_{11}c_{33}) \\ E_3 = \Delta/(c_{12}^2 - c_{11}c_{22}) \end{cases}$$

$$\Delta = c_{33}c_{12}^2 + c_{22}c_{13}^2 + c_{11}c_{23}^2 - c_{11}c_{22}c_{33} - 2c_{12}c_{13}c_{23}$$

$$\begin{cases} v_{12} = (c_{13}c_{23} - c_{12}c_{33})/(c_{23}^2 - c_{22}c_{33}) \\ v_{13} = (c_{12}c_{23} - c_{13}c_{22})/(c_{23}^2 - c_{22}c_{33}) \\ v_{21} = (c_{13}c_{23} - c_{12}c_{33})/(c_{13}^2 - c_{11}c_{33}) \\ v_{23} = (c_{12}c_{13} - c_{11}c_{23})/(c_{13}^2 - c_{11}c_{33}) \\ v_{31} = (c_{12}c_{23} - c_{13}c_{22})/(c_{12}^2 - c_{11}c_{22}) \\ v_{32} = (c_{12}c_{13} - c_{11}c_{23})/(c_{12}^2 - c_{11}c_{22}) \end{cases}$$

$$\begin{cases} E_2 v_{12} = E_1 v_{21} \\ E_3 v_{13} = E_1 v_{31} \\ E_2 v_{32} = E_3 v_{23} \end{cases}$$

$$\begin{cases} \mu_{23} = c_{44} \\ \mu_{13} = c_{55} \\ \mu_{12} = c_{66} \end{cases}$$

where $c_{11}$, $c_{12}$, $c_{13}$, $c_{22}$, $c_{23}$, $c_{33}$, $c_{44}$, $c_{55}$, and $c_{66}$ denote the stiffness coefficients of the orthotropic rock, GPa; $E_1$ denotes a Young's modulus along a direction of a maximum horizontal in-situ stress, GPa; $E_2$ denotes a Young's modulus along a direction of a minimum horizontal in-situ stress, GPa; $E_3$ denotes a Young's modulus along a direction of a vertical in-situ stress, GPa; $v_{12}$ denotes a Poisson's ratio along the direction of the minimum horizontal in-situ stress and perpendicular to the direction of the maximum horizontal in-situ stress; $v_{13}$ denotes a Poisson's ratio along the direction of the vertical in-situ stress and perpendicular to the direction of the maximum horizontal in-situ stress; $v_{21}$ denotes a Poisson's ratio along the direction of the maximum horizontal in-situ stress and perpendicular to the direction of the minimum horizontal in-situ stress; $v_{23}$ a Poisson's ratio along the direction of the vertical in-situ stress and perpendicular to the direction of the minimum horizontal in-situ stress; $v_{31}$ a Poisson's ratio along the direction of the maximum horizontal in-situ stress and perpendicular to the direction of the vertical in-situ stress; and $v_{32}$ denotes a Poisson's ratio along the direction of the minimum horizontal in-situ stress and perpendicular to the direction of the vertical in-situ stress; determining, based on the multiple dynamic elastic parameters of the orthotropic rock, multiple static elastic parameters of the orthotropic rock according to relationships between the multiple dynamic elastic parameters and the multiple static elastic parameters; determining anisotropy Biot coefficients of the orthotropic rock physics model according to the following formulas:

$$\begin{cases} \alpha_{11} = 1 - \dfrac{c_{11}^{dry} + c_{12}^{dry} + c_{13}^{dry}}{c_{11}^m + c_{12}^m + c_{13}^m} \\ \alpha_{22} = 1 - \dfrac{c_{12}^{dry} + c_{22}^{dry} + c_{23}^{dry}}{c_{11}^m + c_{22}^m + c_{23}^m} \\ \alpha_{33} = 1 - \dfrac{c_{13}^{dry} + c_{23}^{dry} + c_{33}^{dry}}{c_{13}^m + c_{23}^m + c_{33}^m} \end{cases}$$

where $c_{11}^{dry}$, $c_{12}^{dry}$, $c_{13}^{dry}$, $c_{22}^{dry}$, $c_{23}^{dry}$, and $c_{33}^{dry}$ denote stiffness coefficients of a dry orthotropic (ORT) rock, GPa; $c_{11}^m$, $c_{12}^m$, $c_{13}^m$, $c_{22}^m$, $c_{23}^m$, and $c_{33}^m$ denote stiffness coefficients of a dry vertical transverse isotropy (VTI) rock, GPa; and $\alpha_{11}$, $\alpha_{22}$, and $\alpha_{33}$ denote the anisotropy Biot coefficients; determining a formation pore pressure based on longitudinal wave time differences according to an Eaton method described as the following formula:

$$P_p = \sigma_v - (\sigma_v - p_w)(AC_n/AC)^c$$

where $\sigma_v$ denotes the vertical in-situ stress, MPa; $p_w$ denotes a formation hydrostatic column pressure, MPa; $AC_n$ denotes a longitudinal wave time difference of trend line at normal pressure, µs/ft; AC denotes an actual longitudinal wave time difference, µs/ft; and $P_p$ denotes the formation pore pressure, MPa; and determining the maximum horizontal in-situ stress and the minimum horizontal in-situ stress of the orthotropic rock according to the following formulas:

$$\begin{cases} \sigma_H = \dfrac{v_{13} + v_{12}v_{23}}{1 - v_{12}v_{21}}(\sigma_v - \alpha_{33}P_p) + \alpha_{11}P_p + \dfrac{E_1}{1 - v_{12}v_{21}}\varepsilon_H + \dfrac{E_1 v_{21}}{1 - v_{12}v_{21}}\varepsilon_h \\ \sigma_h = \dfrac{v_{23} + v_{13}v_{21}}{1 - v_{12}v_{21}}(\sigma_v - \alpha_{33}P_p) + \alpha_{22}P_p + \dfrac{E_2}{1 - v_{12}v_{21}}\varepsilon_h + \dfrac{E_1 v_{21}}{1 - v_{12}v_{21}}\varepsilon_H \end{cases}$$

where $\sigma_H$ denotes the maximum horizontal in-situ stress, MPa; $\sigma_h$ denotes the minimum horizontal in-situ stress, MPa; $\varepsilon_H$ denotes a maximum horizontal strain corresponding to the direction of the maximum horizontal in-situ stress; and $\varepsilon_h$ denotes a minimum horizontal strain corresponding to the direction of the minimum horizontal in-situ stress.

According to yet another aspect of the present disclosure, a method is provided. The method may be implemented on a computing device including at least one processor and at least one storage medium, and a communication platform connected to a network. The method may include obtaining multiple physical parameters of a rock; constructing an orthotropic rock physics model based at least in part on the multiple physical parameters, wherein the orthotropic rock physics model is generated based on a dry matrix rock physics model and a dry organic rock physics model; determining multiple stiffness coefficients based on the orthotropic rock physics model; and determining one or more in-situ stresses of the orthotropic rock based on the multiple stiffness coefficients.

In some embodiments, the multiple physical parameters may be acquired by at least one of well logging, mud logging, or indoor testing.

In some embodiments, the multiple physical parameters of the rock may include compositions of the minerals and the corresponding content thereof, the compositions of the formation fluids and the corresponding content thereof, a porosity of the rock, saturations of the formation fluid.

In some embodiments, the constructing the dry matrix rock physics model may include determining equivalent elastic moduli of matrix minerals based on compositions of the matrix minerals and the corresponding contents thereof; and using an isotropic self-consistent approximation (SCA) model and an isotropic differential effective medium (DEM) model to add inorganic pores to the matrix minerals to construct a dry matrix rock and establish the dry matrix rock physics model.

In some embodiments, the equivalent elastic moduli may include a bulk modulus and a shear modulus. The determining equivalent elastic moduli of matrix minerals based on compositions of the matrix minerals and the corresponding content thereof may include determining a maximum bulk modulus, a minimum bulk modulus, a maximum shear modulus, and a minimum shear modulus of the matrix minerals; designating an average of the maximum bulk modulus and the minimum bulk modulus as the bulk modulus of the matrix minerals; and designating an average of the maximum shear modulus and the minimum shear modulus as the shear modulus of the matrix minerals.

In some embodiments, the constructing the dry organic rock physics model may include determining equivalent elastic moduli of organic materials based on compositions of the matrix minerals and the corresponding contents thereof; determining an equivalent elastic stiffness tensor of an oriented organic rock based on a CL coefficient of the organic minerals; and using an anisotropy DEM model to add organic pores to the oriented organic rock to construct a dry organic rock and establish the dry organic rock physics model.

In some embodiments, the organic minerals may include a plurality of organic particles. The determining an equivalent elastic stiffness tensor of an oriented organic rock based on a CL coefficient of the organic minerals may include determining a deflection angle of each organic particle of a plurality of organic particles in the organic minerals with respect to the axis of symmetry based on scanning electron microscope data of the organic minerals; determining the CL coefficient based on the deflection angle of each organic particle with respect to the axis of symmetry, wherein the CL coefficient represents the arrangement and distribution of the deflection angles of the organic particles of the organic minerals; for organic particles deflected at each angle, determining a stiffness tensor of the corresponding organic particles at the angle by rotating the organic particles to the angle based on Bond transformation; and determining the equivalent elastic stiffness tensor of the oriented organic rock based on the stiffness tensor of each group of organic particles.

In some embodiments, the constructing the orthotropic rock physics model based on the dry matrix rock physics model and the dry organic rock physics model may include constructing a dry VTI rock by adding the dry matrix rock to the dry organic rock based on the anisotropic DEM model to establish a dry VTI rock physics model, constructing a dry orthotropic (ORT) rock by adding vertically distributed fractures to the dry VTI rock based on a gap model to establish a dry ORT rock physics model; and constructing a saturated fluid ORT rock by adding the formation fluids to the dry ORT rock based on a gas saturation and a water saturation to establish the orthotropic rock physics model.

In some embodiments, the determining one or more in-situ stresses of the rock based on the multiple stiffness coefficients may include determining static elastic parameters of the rock based on the multiple stiffness coefficients; determining an anisotropy Biot coefficient in the orthotropic rock physics model; determining a formation pore pressure; and determining the one or more in-situ stresses of the orthotropic rock based on the static elastic parameters, the anisotropic Biot coefficient, and the formation pore pressure.

In some embodiments, the determining static elastic parameters of the rock based on the multiple stiffness coefficients may include determining dynamic elastic parameters based on relationships between stiffness coefficient and dynamic elastic parameter; and determining the static elastic parameters based on the dynamic elastic parameters and relationships between the dynamic elastic parameters and the static elastic parameters.

In some embodiments, the determining each of the relationships between the dynamic elastic parameters and the static elastic parameters may include: determining a dynamic elastic parameter of a core of the rock based on one or more wave speeds of the core; determining a static elastic parameter of the core by performing a rock triaxial compression experiment on the core of the orthotropic rock; and determining the relationship between the dynamic elastic parameter and the static elastic parameter.

According to yet another aspect of the present disclosure, a system is provided. The system may include at least one storage device storing executable instructions, and at least one processor in communication with the at least one storage device. When executing the executable instructions, the at least one processor may cause the system to perform one or more of the following operations. The system may obtain multiple physical parameters of a rock. The system may construct an orthotropic rock physics model based at least in part on the multiple physical parameters, wherein the orthotropic rock physics model is generated based on a dry matrix rock physics model and a dry organic rock physics model. The system may determine multiple stiffness coefficients based on the orthotropic rock physics model. The system may determine one or more in-situ stresses of the orthotropic rock based on the multiple stiffness coefficients.

According to yet another aspect of the present disclosure, a non-transitory computer readable medium storing at least one set of instructions is provided. When executed by at least one processor, the at least one set of instructions may direct the at least one processor to perform a method. The method may include obtaining multiple physical parameters of a rock; constructing an orthotropic rock physics model based at least in part on the multiple physical parameters, wherein the orthotropic rock physics model is generated based on a dry matrix rock physics model and a dry organic rock physics model; determining multiple stiffness coefficients based on the orthotropic rock physics model; and determining one or more in-situ stresses of the orthotropic rock based on the multiple stiffness coefficients.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
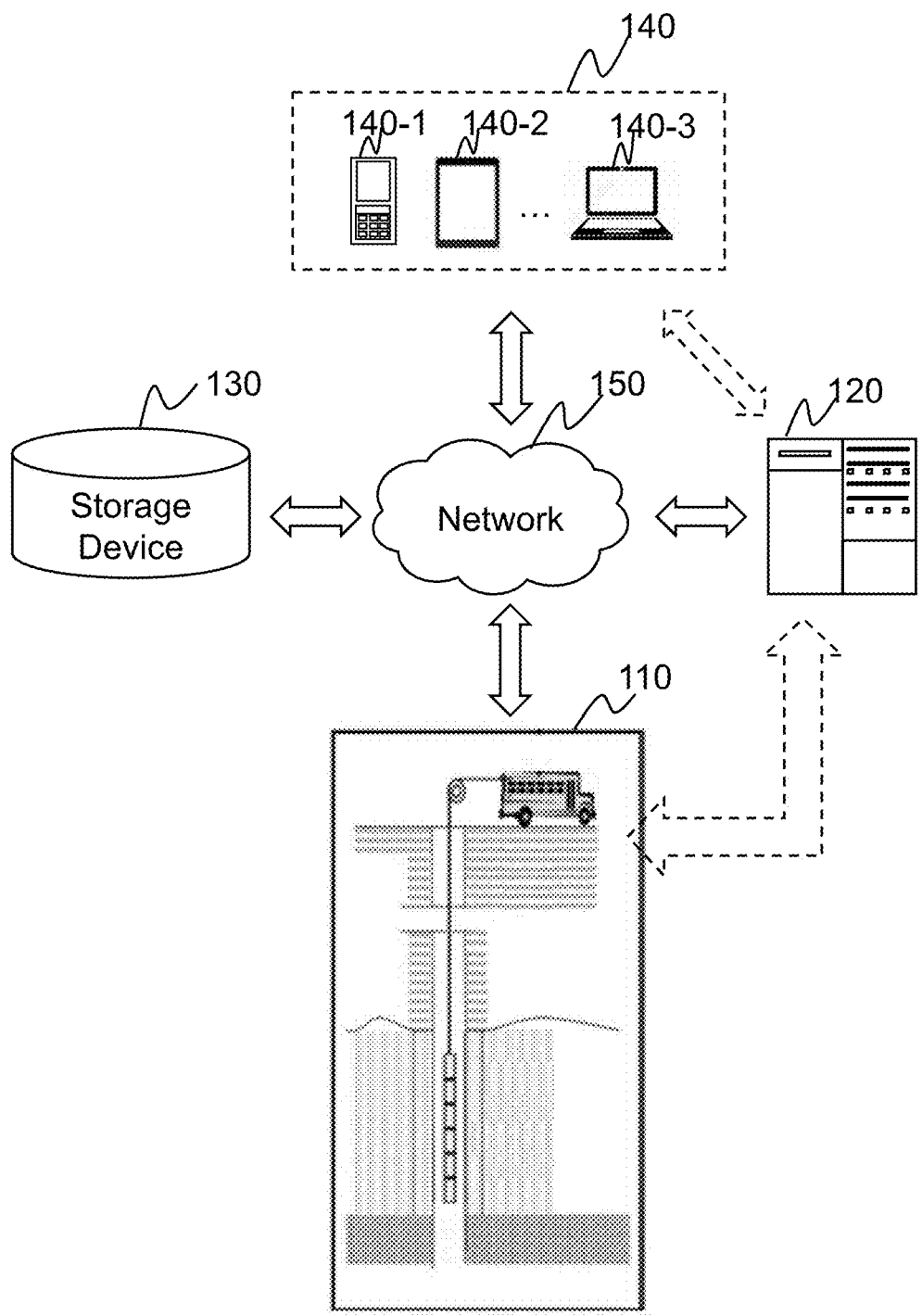
FIG. 1 is a schematic diagram illustrating an exemplary geomechanics prediction system according to some embodiments of the present disclosure.

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown but is to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including" when used in this disclosure, specify the presence of stated features, integers, steps, operations, elements, and/or components, but do not preclude the presence or addition of one or more other features, integers, steps, operations, elements, components, and/or groups thereof.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage devices. In some embodiments, a software module/unit/block may be compiled and linked into an executable program. It will be appreciated that software modules can be callable from other modules/units/blocks or from themselves, and/or maybe invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an erasable programmable read-only memory (EPROM). It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments in the present disclosure. It is to be expressly understood, the operations of the flowchart may be implemented not in order. Conversely, the operations may be implemented in inverted order, or simultaneously. Moreover, one or more other operations may be added to the flowcharts. One or more operations may be removed from the flowcharts.

FIG. 1 is a schematic diagram illustrating an exemplary geomechanics prediction system 100 according to some embodiments of the present disclosure. As shown in FIG. 1, the geomechanics prediction system 100 may include a subterranean measuring device 110, a processing device 120, a storage device 130, a terminal device 140, and a network 150.

The subterranean measuring device 110 may be configured to acquire data relating to a rock. For example, the subterranean measuring device 110 may acquire one or more physical parameter of the rock. In some embodiments, the physical parameter(s) may include composition of the rock and the corresponding content thereof, porosity, saturation, sound wave speed, or the like, or any combination. In some embodiments, the subterranean measuring device 110 may include an inductive device and a ground recording instrument vehicle. The inductive device may be configured to acquire measurement signals. The ground recording instrument vehicle may be configured to collect and detect the signals measured by the inductive device in real time. In some embodiments, the subterranean measuring device 110 may transmit the acquired data relating to the rock to the processing device 120 for analysis and/or application.

The processing device 120 may process data and/or information obtained from the subterranean measuring device 110, the terminal device 140, and/or the storage device 130. In some embodiments, the processing device 120 may be a computer, a user console, a single server or a server group, etc. The server group may be centralized or distributed. In some embodiments, the processing device 120 may be local or remote. For example, the processing device 120 may access information and/or data stored in the subterranean measuring device 110, the terminal device 140, and/or the storage device 130 via the network 150. As another example, the processing device 120 may be directly connected to the subterranean measuring device 110, the terminal device 140 and/or the storage device 130 to access stored information and/or data. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

The storage device 130 may store data, instructions, and/or any other information. In some embodiments, the storage device 130 may store data obtained from the terminal device 140 and/or the processing device 120. In some embodiments, the storage device 130 may store data and/or instructions that the processing device 120 may execute or use to perform exemplary methods/systems described in the present disclosure. In some embodiments, the storage device 130 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more other components in the geomechanics prediction system 100 (e.g., the processing device 120, the terminal device 140, etc.). One or more components in the geomechanics prediction system 100 may access the data or instructions stored in the storage device 130 via the network 150. In some embodiments, the storage device 130 may be directly connected to or communicate with one or more other components in the geomechanics prediction system 100 (e.g., the processing device 120, the terminal device 140, etc.). In some embodiments, the storage device 130 may be part of the processing device 120.

The terminal device 140 may include a mobile device 140-1, a tablet computer 140-2, a laptop computer 140-3, or the like, or any combination thereof. In some embodiments, the mobile device 140-1 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal device 140 may be part of the processing device 120.

The network 150 may include any suitable network that can facilitate the exchange of information and/or data for the geomechanics prediction system 100. In some embodiments, one or more components of the subterranean measuring device 110, the terminal device 140, the processing device 120, the storage device 130, etc., may communicate information and/or data with one or more other components of the geomechanics prediction system 100 via the network 150. For example, the processing device 120 may obtain data from the subterranean measuring device 110 via the network 150. As another example, the processing device 120 may obtain user instructions from the terminal device 140 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the geomechanics prediction system 100 may be connected to the network 150 to exchange data and/or information.

It should be noted that the above description of the geomechanics prediction system 100 is merely provided for the purposes of illustration, and not intended to limit the scope of the present disclosure. For persons having ordinary skills in the art, multiple variations and modifications may be made under the teachings of the present disclosure. For example, the assembly and/or function of the geomechanics prediction system 100 may be varied or changed according to specific implementation scenarios.

Figure 2:
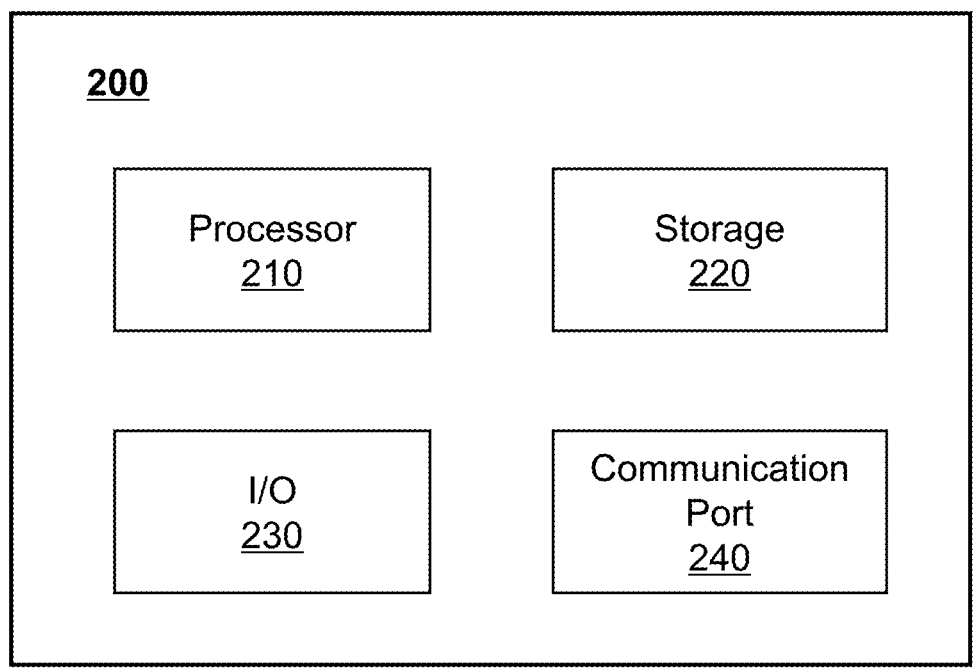
FIG. 2 is a schematic diagram illustrating hardware and/or software components of an exemplary computing device according to some embodiments of the present disclosure.

FIG. 2 is a schematic diagram illustrating hardware and/or software components of an exemplary computing device 200 on which the processing device 120 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (program codes) and perform functions of the processing device 120 in accordance with techniques described herein. The computer instructions may include, for example, routines, programs, objects, components, signals, data structures, procedures, modules, and functions, which perform particular functions described herein. For example, the processor 210 may process data obtained from the subterranean measuring device 110, the terminal device 140, the storage device 130, and/or any other component of the geomechanics prediction system 100. Specifically, the processor 210 may process one or more measured data sets obtained from the subterranean measuring device 110. For example, the processor 210 may construct an orthotropic rock physics model based on the data set(s). In some embodiments, the constructed orthotropic rock physics model may be stored in the storage device 130, the storage 220, etc. In some embodiments, the processor 210 may perform instructions obtained from the terminal device 140. In some embodiments, the processor 210 may include one or more hardware processors, such as a microcontroller, a microprocessor, a reduced instruction set computer (RISC), an application-specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the subterranean measuring device 110, the terminal device 140, the storage device 130, or any other component of the geomechanics prediction system 100. In some embodiments, the storage 220 may include a mass storage device, a removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 120 for determining stresses.

The I/O 230 may input or output signals, data, and/or information. In some embodiments, the I/O 230 may enable user interaction with the processing device 120. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected with a network (e.g., the network 150) to facilitate data communications. The communication port 240 may establish connections between the processing device 120 and the subterranean measuring device 110, the terminal device 140, or the storage device 130. The connection may be a wired connection, a wireless connection, or a combination of both that enables data transmission and reception. The wired connection may include an electrical cable, an optical cable, a telephone wire, or the like, or any combination thereof. The wireless connection may include a Bluetooth network, a Wi-Fi network, a WiMax network, a WLAN, a ZigBee network, a mobile network (e.g., 3G, 4G, 5G, etc.), or the like, or any combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
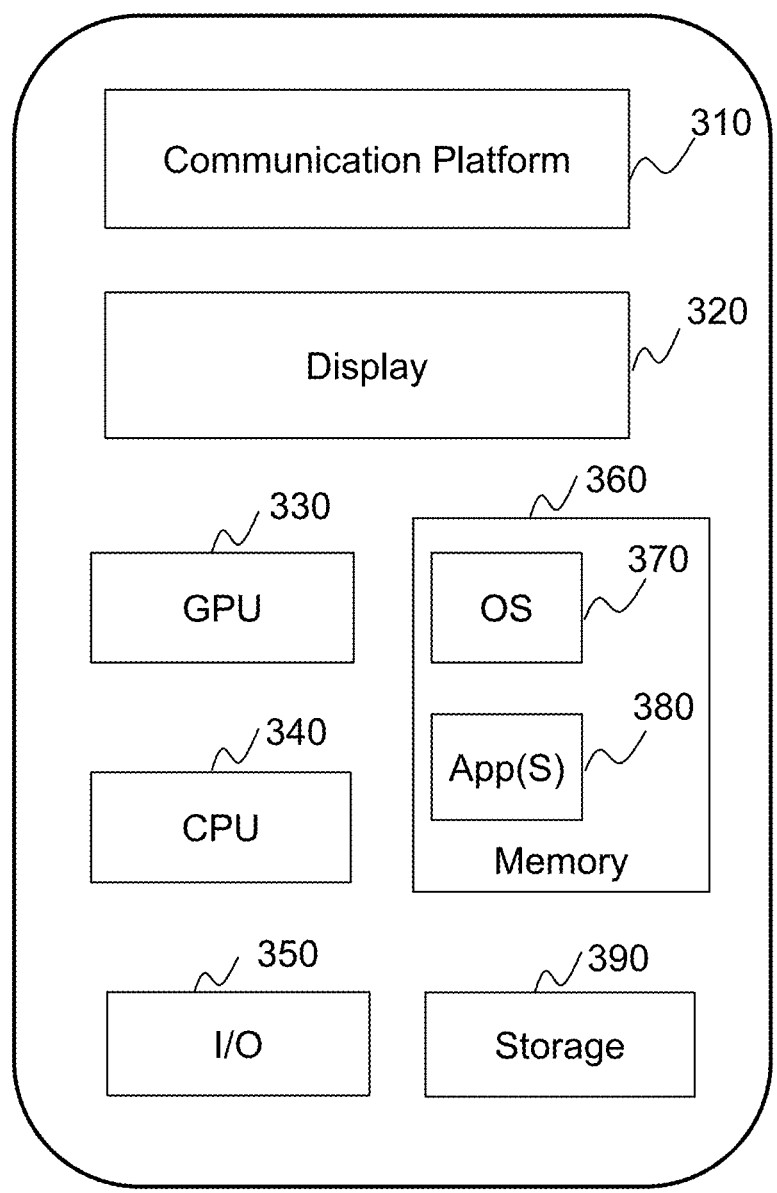
FIG. 3 is a schematic diagram illustrating hardware and/or software components of an exemplary mobile device according to some embodiments of the present disclosure.

FIG. 3 is a schematic diagram illustrating hardware and/or software components of an exemplary mobile device 300 according to some embodiments of the present disclosure. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to stress determination or other information from the processing device 120. User interactions with the information stream may be achieved via the I/O 350 and provided to the processing device 120 and/or other components of the geomechanics prediction system 100 via the network 150.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to construct an orthotropic rock physics model as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4:
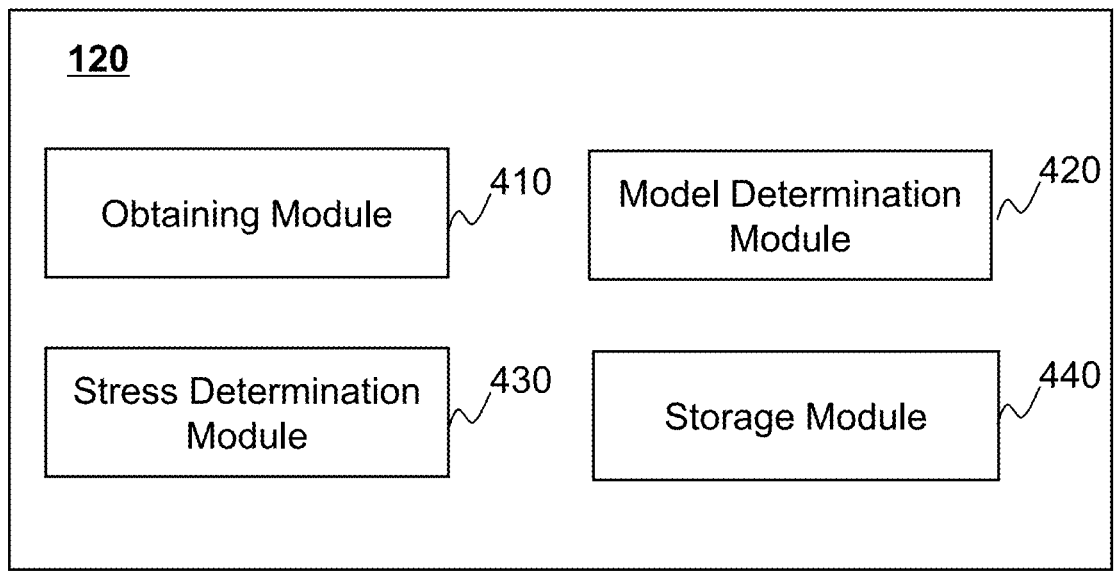
FIG. 4 is a block diagram illustrating an exemplary processing device according to some embodiments of the present disclosure.

FIG. 4 is a block diagram illustrating an exemplary processing device 120 according to some embodiments of the present disclosure. As illustrated in FIG. 4, the processing device 120 may include an obtaining module 410, a model determination module 420, a stress determination module 430, and a storage module 440.

The obtaining module 410 may be configured to obtain physical parameters of a rock. In some embodiments, the rock may be an orthotropic rock.

The model determination module 420 may be configured to construct an orthotropic rock physics model based at least in part on the physical parameters of the rock.

The stress determination module 430 may be configured to determine multiple stiffness coefficients of the orthotropic rock. The stress determination module 430 may further determine one or more in-situ stresses based on the multiple stiffness coefficients. The one or more in-situ stresses may include a maximum horizontal in-situ stress and a minimum horizontal in-situ stress of the orthotropic rock.

The storage module 440 may be configured to store data and/or instructions associated with the geomechanics prediction system 100. For example, the storage module 440 may store data of the orthotropic rock physics model, physics parameters of the rock, etc. In some embodiments, the storage module 440 may be same as the storage device 130 in configuration.

The modules in the processing device 120 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules may be combined as a single module, and any one of the modules may be divided into two or more units. For example, the model determination module 420 and the stress determination module 430 may be integrated into a single module which may determine both the orthotropic rock physics model and the one or more in-situ stresses. As another example, the processing device 120 may further include a transmission module configured to transmit signals (e.g., an electrical signal, an electromagnetic signal) to one or more components (e.g., the terminal device 140) of the geomechanics prediction system 100.

Figure 5:
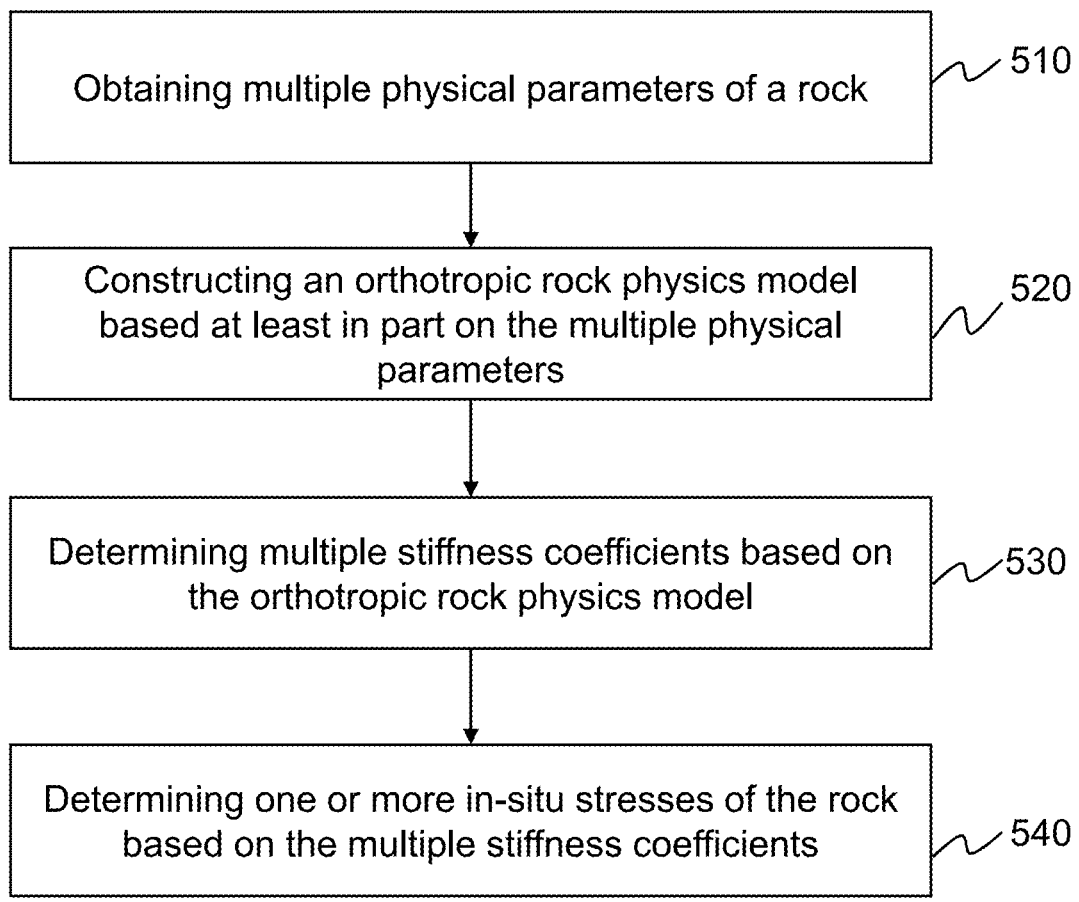
FIG. 5 is a flowchart illustrating an exemplary process for determining in-situ stresses of an orthotropic rock according to some embodiments of the present disclosure.

FIG. 5 is a flowchart illustrating an exemplary process for determining orthotropic stress according to some embodiments of the present disclosure. In some embodiments, process 500 may be implemented as a set of instructions (e.g., an application) stored in a storage device (e.g., the storage device 130, the storage 220, or the storage 390). The processing device 120 (e.g., the processor 210, the CPU 340, or the modules in FIG. 4) may execute the set of instructions, and when executing the instructions, the processing device 120 may be configured to perform the process 500. The operations of the illustrated process presented below are intended to be illustrative. In some embodiments, the process 500 may be accomplished with one or more additional operations not described and/or without one or more of the operations discussed. Additionally, the order in which the operations of the process 500 illustrated in FIG. 5 and described below is not intended to be limiting.

In 510, the processing device 120 (e.g., the obtaining module 410) may obtain multiple physical parameters of a rock.

As used herein, the rock may include minerals, formation fluids, pores (or rock pores), or the like. The minerals may include one or more matrix minerals and/or one or more organic minerals. In some embodiments, the matrix minerals may include quartz, feldspar, calcite, dolomite, pyrite, or the like, or any combination thereof. The organic minerals may include clay, kerogen, or the like, or any combination thereof. In some embodiments, the formation fluid may include water, gas, crude oil, or the like, or any combination thereof. In some embodiments, the rock pores may be divided into inorganic pores and/or organic pores based on a Xu-White model. As used herein, the inorganic pores refers to pores in the matrix minerals, and the organic pores refers to pores in the organic minerals. In some embodiments, the inorganic pores may include intra-granular pores, inter-granular pores, and/or microcracks.

In some embodiments, the multiple physical parameters of the rock may include compositions of the minerals and the corresponding content thereof, the compositions of the formation fluids and the corresponding content thereof, a porosity of the rock, saturations of the formation fluid, or the like, or any combination thereof. For example, when the rock is an orthotropic rock. The multiple physical parameters may include compositions of the matrix minerals, a content of each matrix mineral, compositions of the organic minerals, a content of each organic mineral, a porosity of matrix minerals (or an inorganic porosity), a porosity of organic minerals (or an organic porosity), gas saturation, water saturation, etc.

Figure 7:
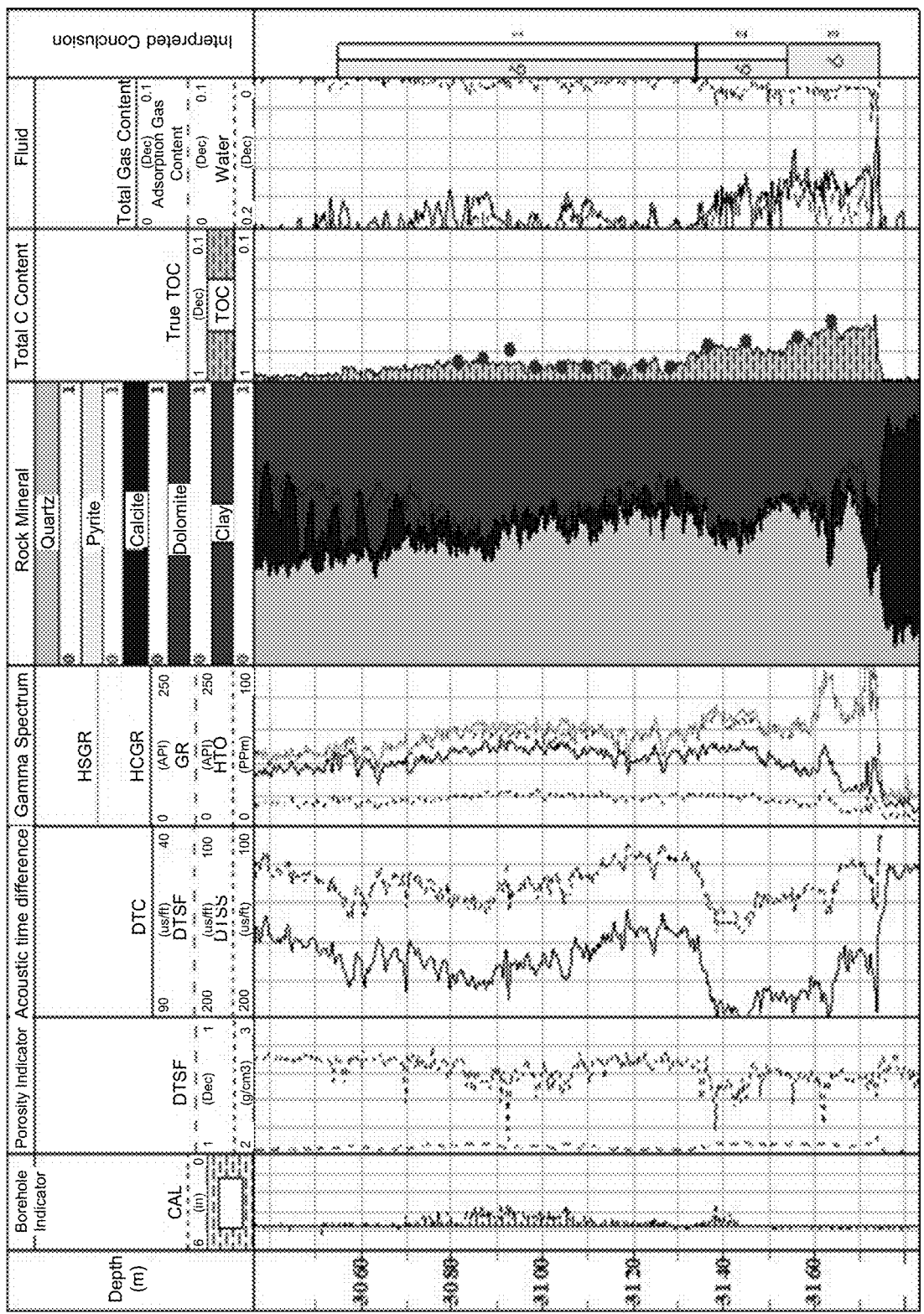
FIG. 7 is a log interpretation diagram of minerals and fluids of a well according to some embodiments of the present disclosure.

In some embodiments, the physical parameter(s) may be acquired by well logging, mud logging, and/or indoor testing. For example, a user may acquire the physical parameter(s) (e.g., as shown in FIG. 7) by well logging, and then store the physical parameter(s) into the storage device 130. The processing device 120 may retrieve the physical parameter(s) from the storage device 130.

In some embodiments, a user can use the indoor testing or well logging to obtain the porosity of rock and the corresponding saturation of the gas and water contained in the rock pores. The gas in rock pores can be divided into adsorbed gas and free gas. The processing device 120 may determine the inorganic porosity and the organic porosity based on relative contents of the free gas and the adsorbed gas. In some embodiments, the content of the adsorbed gas may be calculated by a Langmuir isotherm adsorption equation (Equation (1)) as below:

$$g_a = \frac{V_{1c}p}{p + P_{1t}}, \quad (1)$$

where $g_a$ denotes the content of the adsorbed gas, m³/t; $V_{1c}$ denotes a Langmuir volume after TOC correction at reservoir temperature, m³/t; $P_{1t}$ denotes Langmuir pressure at reservoir temperature, MPa; and p denotes a reservoir pressure, MPa.

In some embodiments, the content of the free gas may be determined based on Equation (2) as below:

$$g_f = \frac{\psi}{\rho B_g}[\emptyset_e(1 - S_w)], \quad (2)$$

where $g_f$ denotes the content of the free gas, m³/t; $\psi$ denotes a constant; $\rho$ denotes a volume density, g/cm³; $B_g$ denotes a gas volume compressibility; $\emptyset_e$ denotes an effective porosity; and $S_w$ denotes an effective saturation;

In some embodiments, the organic porosity and the inorganic porosity may be determined based on Equation (3) as below:

$$\begin{cases} \emptyset_o = \frac{\emptyset g_a}{g_a + g_f} \\ \emptyset_g = \frac{\emptyset g_f}{g_a + g_f}, \end{cases} \quad (3)$$

where $\emptyset_0$ denotes the organic porosity; $\emptyset_g$ denotes the inorganic porosity; $\emptyset$ denotes the porosity of the rock; $g_a$ denotes the content of the adsorbed gas, m³/t; and $g_f$ denotes the content of the free gas, m³/t.

In 520, the processing device 120 (e.g., the model determination module 420) may construct an orthotropic rock physics model based at least in part on the multiple physical parameters.

The orthotropic rock physics model may be generated based on a dry matrix rock physics model and a dry organic rock physics model. In some embodiments, the processing device 120 may determine equivalent elastic moduli of the matrix minerals based on the compositions of the matrix minerals and the corresponding content thereof. The processing device 120 may use an isotropic self-consistent approximation (SCA) model and an isotropic differential effective medium (DEM) model to add the inorganic pores to the matrix minerals to construct a dry matrix rock, and establish the dry matrix rock physics model. In some embodiments, the processing device 120 may use an anisotropic SCA model and an anisotropic DEM model to determine equivalent elastic stiffness tensors of the organic minerals based on the compositions of the organic minerals and the corresponding content thereof. The processing device 120 may determine equivalent elastic stiffness tensors of oriented organic minerals (also referred to as an oriented organic rock) based on a confidence level (CL) coefficient of the organic minerals. The processing device 120 may use the anisotropic DEM model to add the organic pores to the oriented organic minerals to construct a dry organic rock, and establish the dry organic rock physics model.

The processing device 120 may add the dry matrix rock to the dry organic rock to construct a dry vertical transverse isotropy (VTI) rock, and establish a VTI rock physics model based on the dry matrix rock physics model and the dry organic rock physics model using the anisotropic DEM model. The processing device 120 may take the dry VTI rock as the background, and use a fracture model to add vertically distributed fractures to the dry VTI rock to construct a dry orthotropic (ORT) rock, and establish a dry ORT rock physics model. The processing device 120 may add the formation fluid (i.e., mixture of fluids) to the dry ORT rock based on the gas saturation and the water saturation to obtain a saturated fluid rock, and establish the orthotropic rock physics model. More descriptions regarding the determination of the orthotropic rock physics model may be found elsewhere of the present disclosure (e.g., FIG. 6 and the descriptions thereof).

In 530, the processing device 120 (e.g., the stress determination module 430) may determine multiple stiffness coefficients based on the orthotropic rock physics model.

The processing device 120 may determine of transverse wave speeds, longitudinal wave speeds, and/or physical parameters (e.g., bulk density, crack density, crack filling, etc.) of a saturated liquid orthotropic rock based on the orthotropic rock physics model. The multiple stiffness coefficients may be determined based on transverse wave time differences, longitudinal wave time differences, and/or the bulk density of the saturated liquid orthotropic rock. For example, the stiffness coefficients may include $c_{11}$, $c_{12}$, $c_{13}$, $c_{22}$, $c_{23}$, $c_{33}$, $c_{44}$, $c_{55}$, and $c_{66}$, and the multiple stiffness coefficients may be determined based on Equation (4) as below:

$$\begin{cases} c_{11} = \rho_b v_{ph}^2 \\ c_{12} = \rho_b (v_{ph}^2 - 2v_{sh}^2) \\ c_{13} = \rho_b \left[ \left( \left( \frac{4v_{pQ}^2 - v_{ph}^2 - v_{pv}^2 - 2v_{sv}^2}{2} \right)^2 - \left( \frac{v_{ph}^2 - v_{pv}^2}{2} \right)^2 \right)^{1/2} - v_{sv}^2 \right] \\ c_{33} = \rho_b v_{pv}^2 \\ c_{44} = \rho_b v_{sv}^2 \\ c_{55} = C_{44} \\ c_{66} = \frac{C_{11} - C_{12}}{2} \\ c_{22} = c_{11} \\ c_{23} = c_{13} \end{cases} \quad (4)$$

where $\rho_b$ denotes the bulk density of the saturated liquid orthotropic rock, g/cm³; $v_{ph}$ denotes a longitudinal wave speed of parallel bedding planes, km/s; $v_{pQ}$ denotes a longitudinal wave speed at 45° to the bedding planes, km/s; $v_{pv}$ denotes a longitudinal wave speed of vertical bedding planes, km/s; $v_{sh}$ denotes a transverse wave speed of parallel bedding planes, km/s; $v_{sv}$ denotes a transverse wave speed of vertical bedding planes, km/s; $c_{11}$ denotes a longitudinal stiffness coefficient of transverse propagation, GPa; $c_{33}$ denotes a longitudinal stiffness coefficient propagating along a well axis, GPa; $c_{44}$ denotes a transverse stiffness coefficient propagating along a well axis, GPa; $c_{55}$ denotes a transverse stiffness coefficient of longitudinal propagation, GPa; and $c_{66}$ denotes a transverse stiffness coefficient propagating along a horizontal direction, GPa.

In 540, the processing device 120 (e.g., the stress determination module 430) may determine one or more in-situ stresses of the orthotropic rock based on the multiple stiffness coefficients. In some embodiments, the one or more in-situ stresses may include a maximum horizontal in-situ stress and a minimum horizontal in-situ stress of the orthotropic rock.

The processing device 120 may determine static elastic parameters of the orthotropic rock based on the stiffness coefficients. The processing device 120 may determine an anisotropy Biot coefficient in the orthotropic rock physics model based on the orthotropic rock physics model. The processing device 120 may determine a formation pore pressure. The processing device 120 may determine the one or more in-situ stresses of the orthotropic rock based on the static elastic parameters, the anisotropy Biot coefficient, and the formation pore pressure.

In some embodiments, the static elastic parameters may be determined based on dynamic elastic parameters of the orthotropic rock. The dynamic/static elastic parameters may include three Young's moduli, six Poisson's ratios, and three shear moduli. The processing device 120 may determine each dynamic elastic parameter based on a relationship between at least one of the multiple stiffness coefficients and the dynamic elastic parameter. The relationships between the at least one of the multiple stiffness coefficients and the dynamic elastic parameters may be described as Equations (5-9) as below:

$$\begin{cases} E_1 = \Delta/(c_{23}^2 - c_{22}c_{33}) \\ E_2 = \Delta/(c_{13}^2 - c_{11}c_{33}) \\ E_3 = \Delta/(c_{12}^2 - c_{11}c_{22}), \end{cases} \quad (5)$$

-continued $$\Delta = c_{33}c_{12}^2 + c_{22}c_{13}^2 + c_{11}c_{23}^2 - c_{11}c_{22}c_{33} - 2c_{12}c_{13}c_{23}, \quad (6)$$

$$\begin{cases} v_{12} = (c_{13}c_{23} - c_{12}c_{33})/(c_{23}^2 - c_{22}c_{33}) \\ v_{13} = (c_{12}c_{23} - c_{13}c_{22})/(c_{23}^2 - c_{22}c_{33}) \\ v_{21} = (c_{13}c_{23} - c_{12}c_{33})/(c_{13}^2 - c_{11}c_{33}) \\ v_{23} = (c_{12}c_{13} - c_{11}c_{23})/(c_{13}^2 - c_{11}c_{33}) \\ v_{31} = (c_{12}c_{23} - c_{13}c_{22})/(c_{12}^2 - c_{11}c_{22}) \\ v_{32} = (c_{12}c_{13} - c_{11}c_{23})/(c_{12}^2 - c_{11}c_{22}), \end{cases} \quad (7)$$

$$\begin{cases} E_2 v_{12} = E_1 v_{21} \\ E_3 v_{13} = E_1 v_{31} \\ E_2 v_{32} = E_3 v_{23}, \end{cases} \quad (8)$$

$$\begin{cases} \mu_{23} = c_{44} \\ \mu_{13} = c_{55} \\ \mu_{12} = c_{66}, \end{cases} \quad (9)$$

where E (including $E_1$, $E_2$, and $E_3$) denotes a Young's modulus, GPa; v (including $v_{12}$, $v_{13}$, $v_{21}$, $v_{23}$, $v_{31}$, and $v_{32}$) denotes a Poisson's ratio; and $\mu$ (including $\mu_{12}$, $\mu_{13}$, and $\mu_{23}$) denotes a shear modulus, GPa.

The processing device 120 may determine each of the static elastic parameters based on a dynamic-static conversion relationship of rock elastic parameter.

In some embodiments, for a specific static elastic parameter, a dynamic-static conversion relationship corresponding to the specific static elastic parameter may be determined based on a rock triaxial compression experiment. For example, the rock triaxial compression experiment may be performed on a core of the rock to obtain a static elastic parameter of the core. The processing device 120 may determine a dynamic elastic parameter of the core based on wave speed characteristics (e.g., an acoustic velocity of the core) of the rock. The processing device 120 may determine the dynamic-static conversion relationship of rock elastic parameter based on the dynamic elastic parameter of the core and the static elastic parameter of the core. Specifically, during the rock triaxial compression experiment, an initial confining pressure may be first given to a sample rock, and then an axial pressure may be gradually applied until the sample rock is broken. During the experiment, a recording device may automatically record a relationship curve among a force of the sample rock, a longitudinal strain, and a transverse strain under various confining pressure conditions. A stress-strain relationship curve of the sample rock may be determined based on the relationship curve of force, longitudinal strain, and lateral strain of the sample rock and a size of the sample rock. The processing device 120 may determine the static elastic parameter of the core according to the stress-strain relationship curve.

In some embodiments, the anisotropy Biot coefficients may be determined based on a drainage technique, a sonic technique, or the like, or any combination thereof. For example, the processing device 120 may directly determine the anisotropy Biot coefficients based on acoustic wave time difference. As another example, the processing device 120 may determine the anisotropy Biot coefficients based on the stiffness matrix. In some embodiments, the anisotropy Biot coefficients may be determined based on Equation (10) as below:

$$\begin{cases} \alpha_{11} = 1 - \dfrac{c_{11}^{dry} + c_{12}^{dry} + c_{13}^{dry}}{c_{11}^m + c_{12}^m + c_{13}^m} \\ \alpha_{22} = 1 - \dfrac{c_{12}^{dry} + c_{22}^{dry} + c_{23}^{dry}}{c_{11}^m + c_{22}^m + c_{23}^m} \\ \alpha_{33} = 1 - \dfrac{c_{13}^{dry} + c_{23}^{dry} + c_{33}^{dry}}{c_{13}^m + c_{23}^m + c_{33}^m}, \end{cases} \quad (10)$$

where $c_{11}^{dry}$, $c_{12}^{dry}$, $c_{13}^{dry}$, $c_{22}^{dry}$, $c_{23}^{dry}$, and $c_{33}^{dry}$ denote stiffness coefficients of the dry ORT rock, GPa; $c_{11}^m$, $c_{12}^m$, $c_{13}^m$, $c_{22}^m$, $c_{23}^m$, and $c_{33}^m$ denote stiffness coefficients of the dry VTI rock, GPa; and $\alpha_{11}$, $\alpha_{22}$, and $\alpha_{33}$ denote the anisotropy Biot coefficients.

In some embodiments, techniques used to determine the formation pore pressure may include an equivalent depth technique, an Eaton technique, an effective stress technique, a Bowers technique, an empirical statistics technique, or the like, or any combination thereof. For example, the processing device 120 may determine the formation pore pressure based on longitudinal wave time differences according to the Eaton technique (Equation (11)) as below:

$$P_p = \sigma_v - (\sigma_v - p_w)(AC_n - AC)^c, \quad (11)$$

where $\sigma_v$ denotes a vertical in-situ stress, MPa; $p_w$ denotes a formation hydrostatic column pressure, MPa; $AC_n$ denotes a longitudinal wave time difference of trend line at normal pressure, μs/ft; AC denotes an actual longitudinal wave time difference, μs/ft; $P_p$ denotes the formation pore pressure, MPa; and c denotes an Eaton index.

In some embodiments, the processing device 120 may determine the one or more in-situ stresses based on Equation (12) as below:

$$\begin{cases} \sigma_H = \dfrac{v_{13} + v_{12}v_{23}}{1 - v_{12}v_{21}}(\sigma_v - \alpha_{33}P_p) + \alpha_{11}P_p + \dfrac{E_1}{1 - v_{12}v_{21}}\varepsilon_H + \dfrac{E_1 v_{21}}{1 - v_{12}v_{21}}\varepsilon_h \\ \sigma_h = \dfrac{v_{23} + v_{13}v_{21}}{1 - v_{12}v_{21}}(\sigma_v - \alpha_{33}P_p) + \alpha_{22}P_p + \dfrac{E_2}{1 - v_{12}v_{21}}\varepsilon_h + \dfrac{E_1 v_{21}}{1 - v_{12}v_{21}}\varepsilon_H, \end{cases} \quad (12)$$

where $\sigma_H$ denotes the maximum horizontal in-situ stress, MPa; $\sigma_h$ denotes the minimum horizontal in-situ stress, MPa; $\varepsilon_H$ denotes a maximum horizontal strain corresponding to a direction of the maximum horizontal in-situ stress; and $\varepsilon_h$ denotes a minimum horizontal strain corresponding to a direction of the minimum horizontal in-situ stress.

It should be noted that the above descriptions are merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 6:
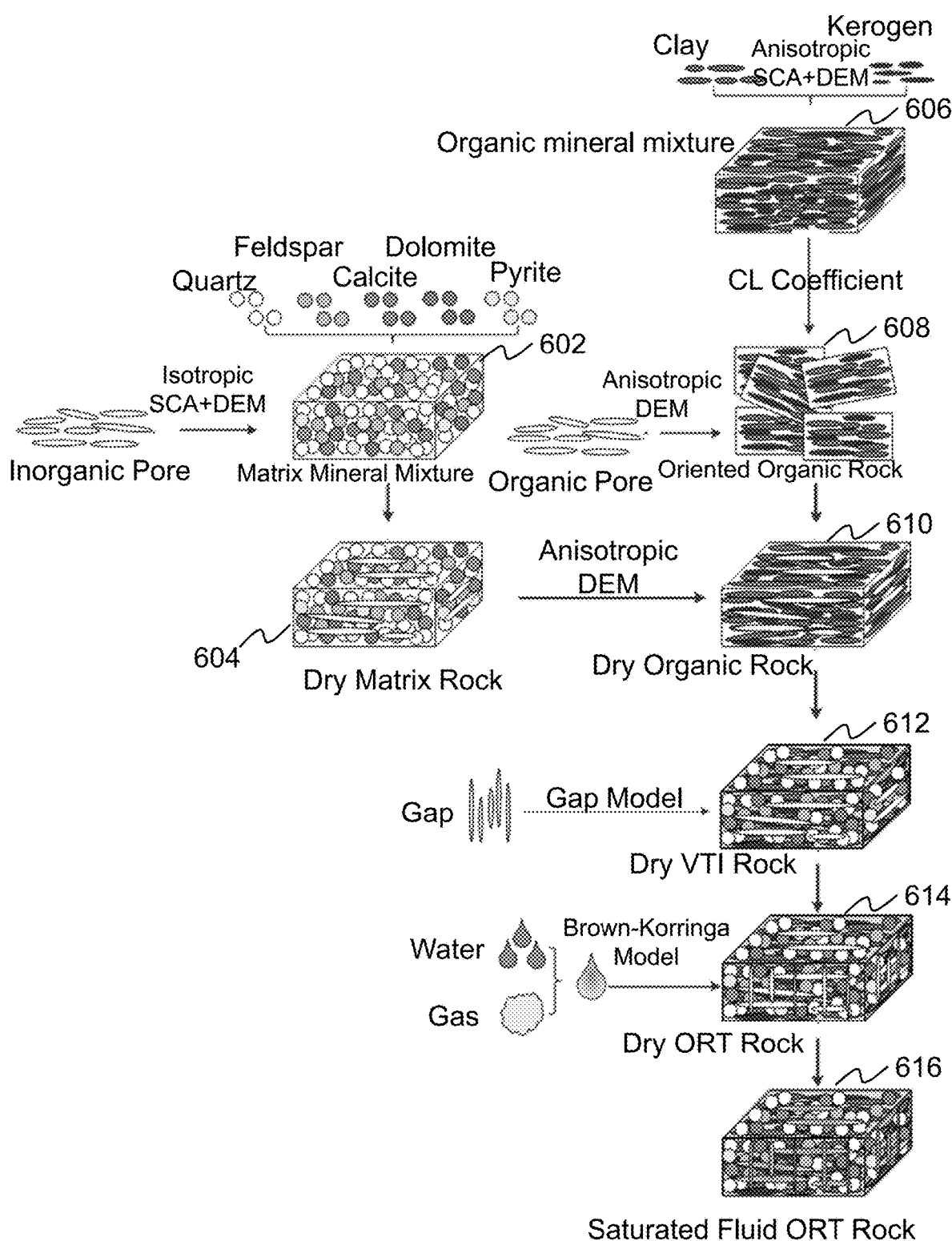
FIG. 6 is a flowchart illustrating an exemplary process for constructing an orthotropic rock physics model according to some embodiments of the present disclosure.

FIG. 6 is a flowchart illustrating an exemplary process for constructing an orthotropic rock physics model according to some embodiments of the present disclosure. The orthotropic rock physics model may be generated based on a dry matrix rock physics model and a dry organic rock physics model.

The dry matrix rock physics model may be constructed based on matrix minerals and inorganic pores. For example, as shown in FIG. 6, the matrix minerals may include quartz, feldspar, calcite, dolomite, and pyrite. The processing device 120 may determine a matrix mineral mixture 602 based on the compositions of the matrix minerals and the corresponding content of each mineral. The processing device 120 may determine an equivalent elastic modulus of the matrix mineral mixture 602. The processing device 120 may use an isotropic SCA model and an isotropic DEM model to add the inorganic pores to the matrix mineral mixture 602 to construct a dry matrix rock 604 and establish the dry matrix rock physics model.

In some embodiments, the equivalent elastic modulus of the matrix mineral mixture 602 may include a bulk modulus and a shear modulus. The processing device 120 may determine a maximum bulk modulus, a minimum bulk modulus, a maximum shear modulus, and a minimum shear modulus of the matrix mineral mixture 602. The processing device 120 may designate an average of the maximum bulk modulus and the minimum bulk modulus as the bulk modulus of the matrix mineral mixture 602. The processing device 120 may designate an average of the maximum shear modulus and the minimum shear modulus as the shear modulus of the matrix mineral mixture 602. For example, the processing device 120 may determine the maximum bulk modulus, the minimum bulk modulus, the maximum shear modulus, and the minimum shear modulus based on a Hashin-Shtrikman bounds (Equation (13)) described as below:

$$\begin{cases} K^{HS+} = \Lambda(\mu_{max}), K^{HS-} = \Lambda(\mu_{min}) \\ \mu^{HS+} = \Gamma(\zeta(K_{max}, \mu_{max})), \mu^{HS-} = \Gamma(\zeta(K_{min}, \mu_{min})), \end{cases} \quad (13)$$

where $K^{HS+}$ denotes the maximum bulk modulus, GPa; $K^{HS-}$ denotes the minimum bulk modulus, GPa; $\mu^{HS+}$ denotes the maximum shear modulus, GPa; and $\mu^{HS-}$ denotes the minimum shear modulus, GPa.

In some embodiments, the processing device 120 may determine an equivalent elastic tensor of the dry matrix rock 604 based on the dry matrix rock physics model. For example, the processing device 120 may acquire a critical porosity of the dry matrix rock 604. The processing device 120 may determine a bulk modulus and a shear modulus of the day matrix rock 604 based on an isotropic SCA model and an isotropic DEM model when the porosity of the day matrix rock 604 is the critical porosity. The processing device 120 may adjust the porosity of the dry matrix 604 from the critical porosity to an inorganic porosity $Ø_g$ based on the isotropic DEM model. Then a bulk modulus and a shear modulus of the day matrix rock 604 when the porosity of the day matrix rock 604 is the organic porosity $Ø_g$ may be determined.

In some embodiments, the isotropic SCA model may be described as Equation (14) as below:

$$\begin{cases} \sum_{i=1}^{N} v_i(K_i - K_{SCA}^+)P^{+i} = 0 \\ \sum_{i=1}^{N} v_i(\mu_i - \mu_{SCA}^+)Q^{+i} = 0 \end{cases} \quad (14)$$

where $v_i$ denotes a volume fraction of the i-th mineral; $P^{+i}$ denotes a first geometric factor of the i-th mineral; $Q^{+i}$ denotes a second geometric factor of the i-th mineral; $K_{SCA}^+$ denotes an equivalent bulk modulus, GPa; and $\mu_{SCA}^+$ denotes an equivalent shear modulus, GPa.

In some embodiments, the isotropic DEM model may be described as Equation (15) as below:

$$\begin{cases} (1-v)\frac{d}{dv}[K^+(v)] = (K_2 - K^+)P^{(+2)}(v) \\ (1-v)\frac{d}{dv}[\mu^+(v)] = (\mu_2 - \mu^+)Q^{(+2)}(v), \end{cases} \quad (15)$$

where $K_1$ denotes a bulk modulus of a background medium, GPa; $\mu_1$ denotes a shear modulus of the background medium, GPa; $K_2$ denotes a bulk modulus of an inclusion, GPa; $\mu_2$ a shear modulus of the inclusion, GPa; v denotes a volume fraction of the inclusion; and an initial condition satisfies that $K^+(0)=K_1$, and $\mu^+(0)=\mu_1$.

The dry organic rock physics model may be constructed based on organic minerals and organic pores. For example, as shown in FIG. 6, the organic minerals may include clay and kerogen. The processing device 120 may determine an organic mineral mixture 606 based on the compositions of the organic minerals and the corresponding content of each mineral based on an anisotropy SCA model and an anisotropy DEM model. The processing device 120 may determine an equivalent elastic stiffness tensor of the organic mineral mixture 606. The processing device 120 may determine an equivalent elastic stiffness tensor of an oriented organic rock 608 based on a CL coefficient of the organic mineral mixture 606. The processing device 120 may use the anisotropy DEM model to add the organic pores to the oriented organic rock 608 to construct a dry organic rock 610 and establish the dry organic rock physics model.

In some embodiments, in order to obtain the equivalent elastic stiffness tensor of the organic mineral mixture 606, the processing device 120 may first use the anisotropic SCA model to determine elastic characteristics of the organic mineral mixture 606 when the content of each substance in the organic mineral mixture 606 is equal. The processing device 120 may then use the anisotropic DEM model to adjust the content (e.g., volume content) of each substance to the corresponding percentage to obtain the equivalent elastic stiffness tensor of the organic mineral mixture 606. For example, when the organic minerals just include kerogen and clay, the processing device 120 may use the anisotropic SCA model to calculate elastic characteristics when the content of kerogen and clay each account for 50%. The processing device 120 may use the anisotropic DEM model to adjust the volume content of the kerogen and clay to the corresponding content percentage. In such cases, it not only ensures the interconnection of kerogen and clay, but also avoids the asymmetry of elastic modulus of the organic mineral mixture 606 due to the different order of addition of kerogen and clay.

In some embodiments, the anisotropy SCA model may be described as Equation (16) as below:

$$\tilde{C}_{ijkl}^{SCA} = \sum_{n=l}^{N} v_n \tilde{C}_{ijkl}^n (\tilde{I}_{ijkl} + \tilde{G}_{ijkl}^n (\tilde{C}_{ijkl}^n - \tilde{C}_{ijkl}^{SCA}))^{-1} \quad (16)$$

-continued $$\left\{\sum_{p=1}^{N} v_P\left(\tilde{I}_{ijkl} + \tilde{G}_{ijkl}^P\left(\tilde{C}_{ijkl}^P - \tilde{C}_{ijkl}^{SCA}\right)\right)^{-1}\right\}^{-1},$$

where $\tilde{C}_{ijkl}^{SCA}$ denotes an equivalent stiffness tensor of the anisotropy SCA model, GPa; $\tilde{G}_{kl}$ denotes an Eshelby stiffness tensor of the n-th material, GPa; $\tilde{I}_{ijkl}$ denotes a fourth-order unit stiffness tensor; $\tilde{C}_{ijkl}^n$ denotes a stiffness tensor of the n-th mineral, GPa; and $v_n$ denotes a volume fraction of the n-th mineral.

In some embodiments, the anisotropy DEM model may be described as Equation (17) as below:

$$\frac{d}{dv}\left(\tilde{C}_{ijkl}^{DEM}(v)\right) = \frac{1}{(1-v)}\left(\tilde{C}_{ijkl}^{I} - \tilde{C}_{ijkj}^{DEM}(v)\right)\left[\tilde{I}_{ijkl} + \tilde{G}_{ijkl}^{I}\left(\tilde{C}_{ijkl}^{P} - \tilde{C}_{ijkl}^{DEM}(v)\right)\right]^{-1}, \quad (17)$$

where $\tilde{C}_{ijkl}^{DEM}$ denotes a stiffness tensor of the background medium, GPa; $\tilde{C}_{ijkl}^{I}$ denotes a stiffness tensor of the inclusion, GPa; $\tilde{G}_{ijkl}^{I}$ denotes an Eshelby stiffness tensor of the inclusion; $\tilde{I}_{ijkl}$ denotes the fourth order unit stiffness tensor; and v denotes a volume fraction of a material being added, decimal.

In some embodiments, in order to obtain the CL coefficient of the organic mineral mixture 606, the processing device 120 may determine a deflection angle of each organic particle of a plurality of organic particles in the organic mineral mixture 606 with respect to the axis of symmetry based on scanning electron microscope data of the organic mineral mixture 606. The processing device 120 may determine the CL coefficient based on the deflection angle of each organic particle with respect to the axis of symmetry. The CL coefficient may represent the arrangement and distribution of the deflection angles of the organic particles of the organic mineral mixture 606. For organic particles deflected at a specific angle, the processing device 120 may determine a stiffness tensor of the corresponding organic particles at the specific angle by rotating the oriented organic particles to the corresponding deflection angle (i.e., the specific angle) based on Bond transformation. The processing device 120 may determine the equivalent elastic stiffness tensor of the oriented organic rock 608 based on the stiffness tensor of each group of organic particles. In some embodiments, the processing device 120 may superimpose the stiffness tensor of each group of organic particles using a V-R-H model.

In some embodiments, a measure result of elastic moduli of minerals and fluids may be listed in Table 1.

TABLE 1

Elastic moduli of minerals and fluids

| Physical parameter | K(GPa) | μ(GPa) | Density (g/cm³) |
|---|---|---|---|
| Quartz | 37 | 4 | 2.65 |
| Calcite | 76.8 | 32 | 2.71 |
| Feldspar | 75.6 | 25.6 | 2.63 |
| Dolomite | 94.9 | 45 | 2.87 |
| Pyrite | 147.4 | 132.5 | 4.93 |
| Clay | 25 | 9 | 2.55 |
| Kerogen | 2.9 | 2.7 | 1.3 |
| Water | 2.2 | 0 | 1.04 |
| Gas | 0.01 | 0 | 0.1 |

The processing device 120 may construct the orthotropic rock physics model based on the dry matrix rock physics model and the dry organic rock physics model. For example, the processing device 120 may construct a dry VTI rock 612 by adding the dry matrix rock 604 to the dry organic rock 610 based on the anisotropic DEM model to establish a dry VTI rock physics model and determine an elastic tensor of the dry VTI rock 612. The processing device 120 may designate the dry VTI rock 612 as a background medium, and then construct a dry orthotropic (ORT) rock 614 by adding vertically distributed fractures (or gaps) to the dry VTI rock 612 based on a gap model to establish a dry ORT rock physics model. The processing device 120 may construct a saturated fluid ORT rock 616 by adding the formation fluids to the dry ORT rock 614 based on a gas saturation and a water saturation.

In some embodiments, the gap model may include an anisotropy Schoenberg linear sliding model, a Hudson model, or the like, or any combination thereof. For example, the anisotropy Schoenberg linear sliding model may be described as Equation (18) as below:

$$C = \begin{bmatrix} c_{11b} - \frac{\Delta_N c_{12b}^2}{c_{11b}} & c_{12b}(1-\Delta_N) & c_{13b}\left(1 - \frac{\Delta_N c_{12b}}{c_{11b}}\right) & 0 & 0 & 0 \\ c_{12b}(1-\Delta_N) & c_{11b}(1-\Delta_N) & c_{13b}(1-\Delta_N) & 0 & 0 & 0 \\ c_{13b}\left(1 - \frac{\Delta_N c_{12b}}{c_{11b}}\right) & c_{13b}(1-\Delta_N) & c_{33b}\left(1 - \frac{\Delta_N c_{13b}^2}{c_{11b}}\right) & 0 & 0 & 0 \\ 0 & 0 & 0 & c_{44b} & 0 & 0 \\ 0 & 0 & 0 & 0 & c_{44b}(1-\Delta_V) & 0 \\ 0 & 0 & 0 & 0 & 0 & c_{66b}(1-\Delta_H) \end{bmatrix}, \quad (18)$$

where C denotes a stiffness matrix of the dry ORT rock after adding the vertically distributed fractures, GPa; $c_{11b}$, $c_{12b}$, $c_{13b}$, $c_{33b}$, $c_{44b}$, and $c_{66b}$ denote stiffness coefficients of the dry VTI rock without the vertically distributed fractures, GPa; and $\Delta_N$, $\Delta_V$, and $\Delta_H$ denote weak degrees of characteristics of the vertically distributed fractures.

In some embodiments, the processing device 120 may determine and convert a bulk modulus of gas-water mixture in the pores (e.g., the organic pores and/or the organic pores) into a stiffness tensor based on a Wood formula according to the gas saturation and the water saturation. By combining with orthotropic nature of the dry ORT rock, the processing device 120 may construct the saturated fluid ORT rock by adding the formation fluids to the dry ORT rock based on a Brown-Korringa model to establish the orthotropic rock physics model.

In some embodiments, the Wood formula (Equation (19)) may be described as below:

$$\begin{cases} K_f = \dfrac{K_g K_w}{S_g K_w + (1-S_g)_{K_g}} \\ \mu_f = 0 \end{cases} \quad (19)$$

where $K_g$ denotes a bulk modulus of gas, GPa; $K_w$ denotes a bulk modulus of water, GPa; $K_f$ denotes an equivalent bulk modulus of mixed fluids (or formation fluids), GPa; $S_g$ denotes the gas saturation; and $\mu_f$ denotes an equivalent shear modulus of the mixed fluid, GPa.

In some embodiments, the Brown-Korringa model may be described as Equation (20) as below:

$$S_{ijkl}^{sat} = S_{ijkl}^{dry} - \dfrac{(s_{ijmm}^{dry} - s_{ijmm}^{gr})(s_{nnkl}^{dry} - s_{nnkl}^{gr})}{(s_{aabb}^{dry} - s_{aabb}^{gr}) + \emptyset(\beta_{fl} - \beta_{gr})}, \quad (20)$$

where $S_{ijkl}^{sat}$ denotes a flexibility tensor of the saturated fluid ORT rock, GPa$^{-1}$; $S_{ijkl}^{dry}$ denotes a flexibility tensor of the dry ORT rock, GPa$^{-1}$; $S_{ijmm}^{gr}$ denotes a flexibility tensor of the dry VTI rock, GPa$^{-1}$; $\beta_{fl}$ denotes a compressibility factor of the mixed fluids; $\beta_{gr}$ denotes a compressibility factor of the minerals, GPa$^{-1}$; and $\emptyset$ denotes a porosity.

It should be noted that the above descriptions are merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

FIG. 7 is a log interpretation diagram of minerals and fluids of a well according to some embodiments of the present disclosure. According to FIG. 7, multiple physical parameters of rock in the well may be obtained and an orthotropic rock physics model may be constructed based on the multiple physical parameters.

Figure 8:
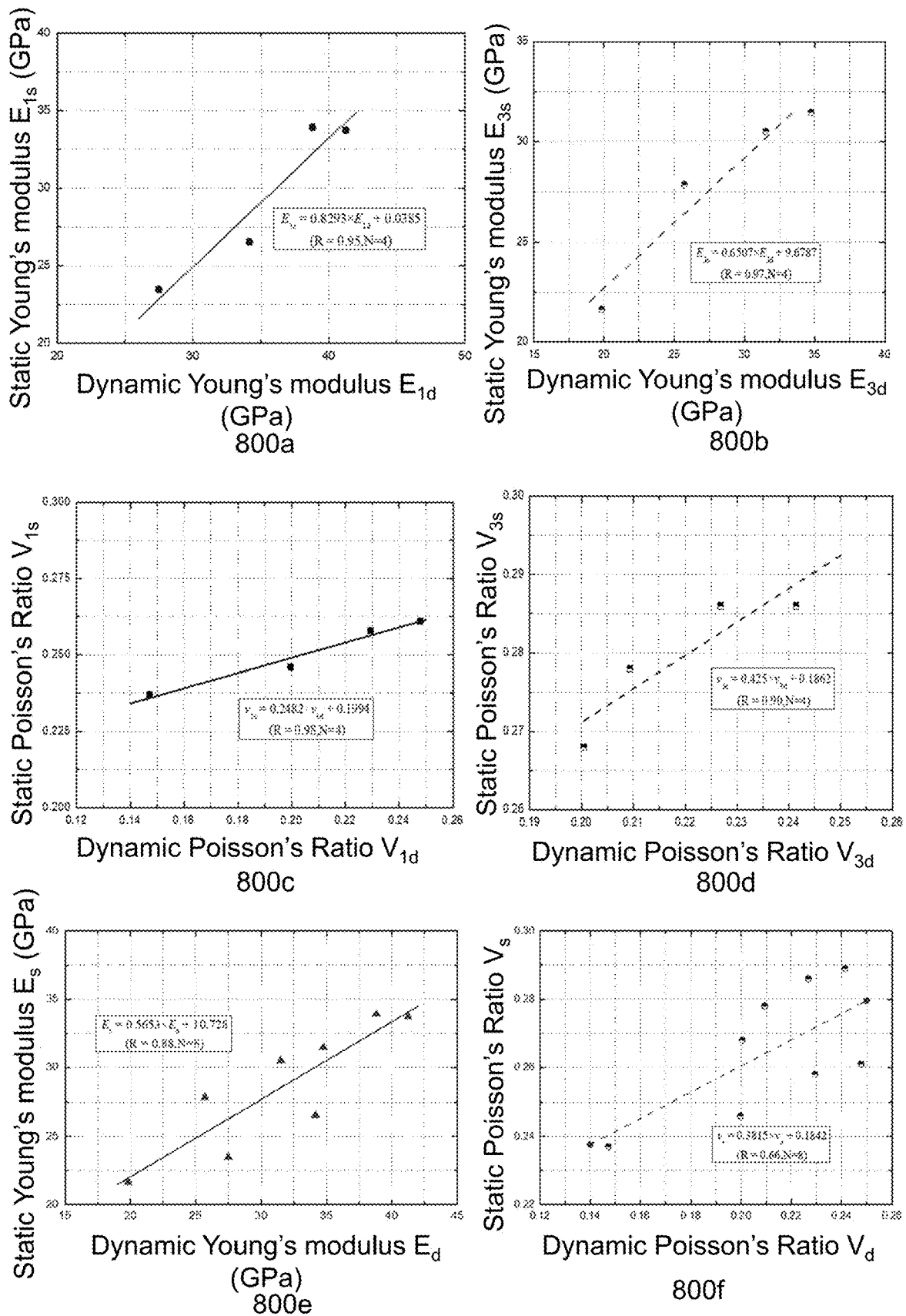
FIG. 8 illustrates dynamic-static relationship charts of rock elastic parameters according to some embodiments of the present disclosure.

FIG. 8 illustrates dynamic-static relationship charts of rock elastic parameters according to some embodiments of the present disclosure. Chart 800a represents a dynamic-static relationship between a dynamic Young's modulus $E_{1d}$ and a static Young's modulus $E_{1s}$. Chart 800b represents a dynamic-static relationship between a dynamic Young's modulus $E_{3d}$ and a static Young's modulus $E_{3s}$. Chart 800c represents a dynamic-static relationship between a dynamic Poisson's ratio $v_{1d}$ and a static Poisson's ratio $v_{1s}$. Chart 800d represents a dynamic-static relationship between a dynamic Poisson's ratio $v_{3d}$ and a static Poisson's ratio $v_{3s}$. Chart 800e represents a total dynamic-static relationship between a dynamic Young's modulus $E_d$ and a dynamic Young's modulus $E_s$. Chart 800f represents a total dynamic-static relationship between a dynamic Poisson's ratio $v_d$ and a static Poisson's ratio $v_s$. A static elastic parameter may be determined based on a dynamic elastic parameter and the dynamic-static relationships of elastic parameter.

Figure 9:
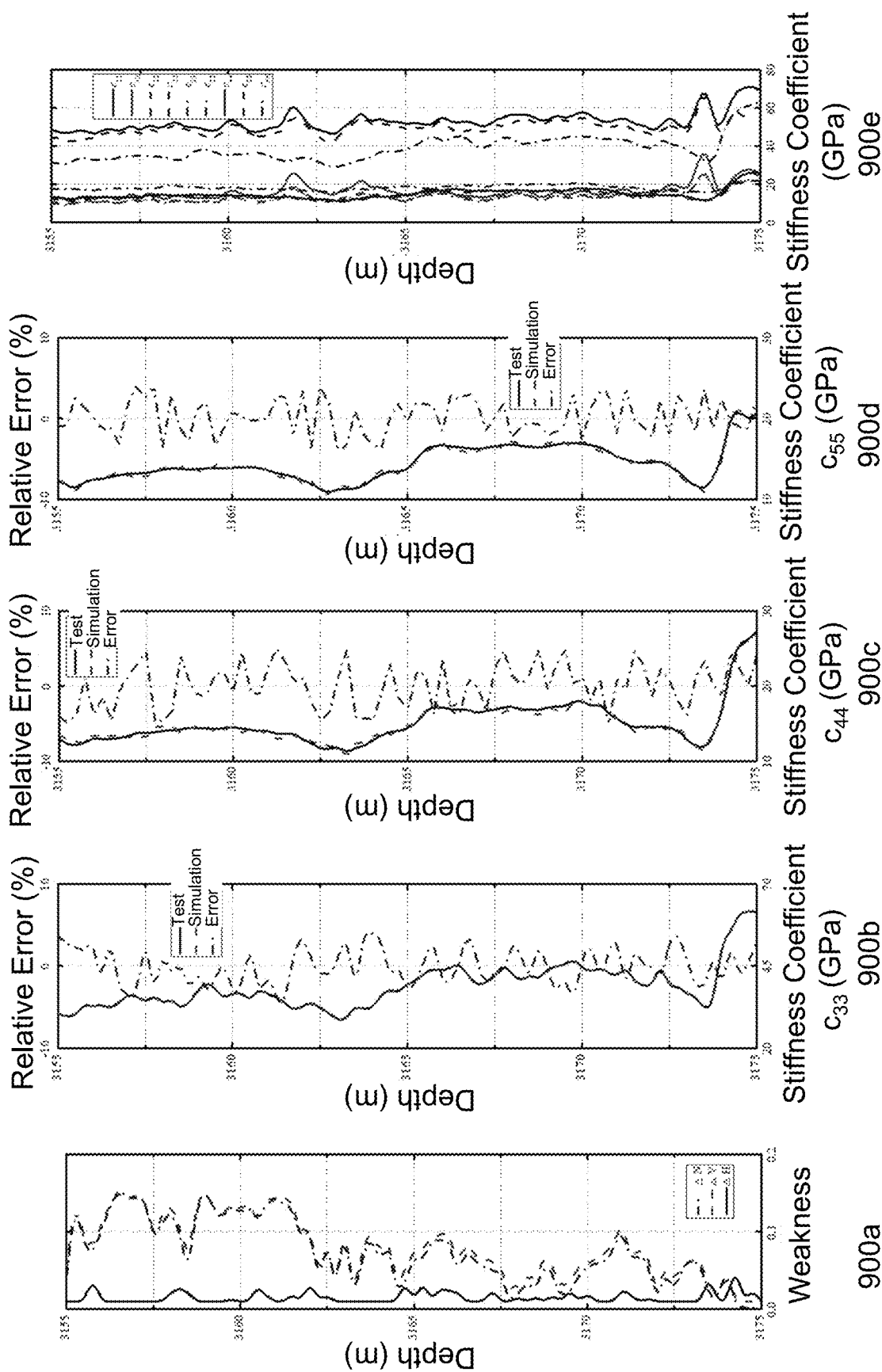
FIG. 9 illustrates comparing results of stiffness coefficients obtained based on different methods according to some embodiments of the present disclosure.

FIG. 9 illustrates comparing results of stiffness coefficients obtained based on different methods according to some embodiments of the present disclosure. Chart 900a represents a weak degree of gaps in the rock. According to Chart 900b-900d, stiffness coefficients determined based on an orthotropic rock physics model may have a close to the stiffness coefficients obtained by well logging, and errors are less than 10%.

Figure 10:
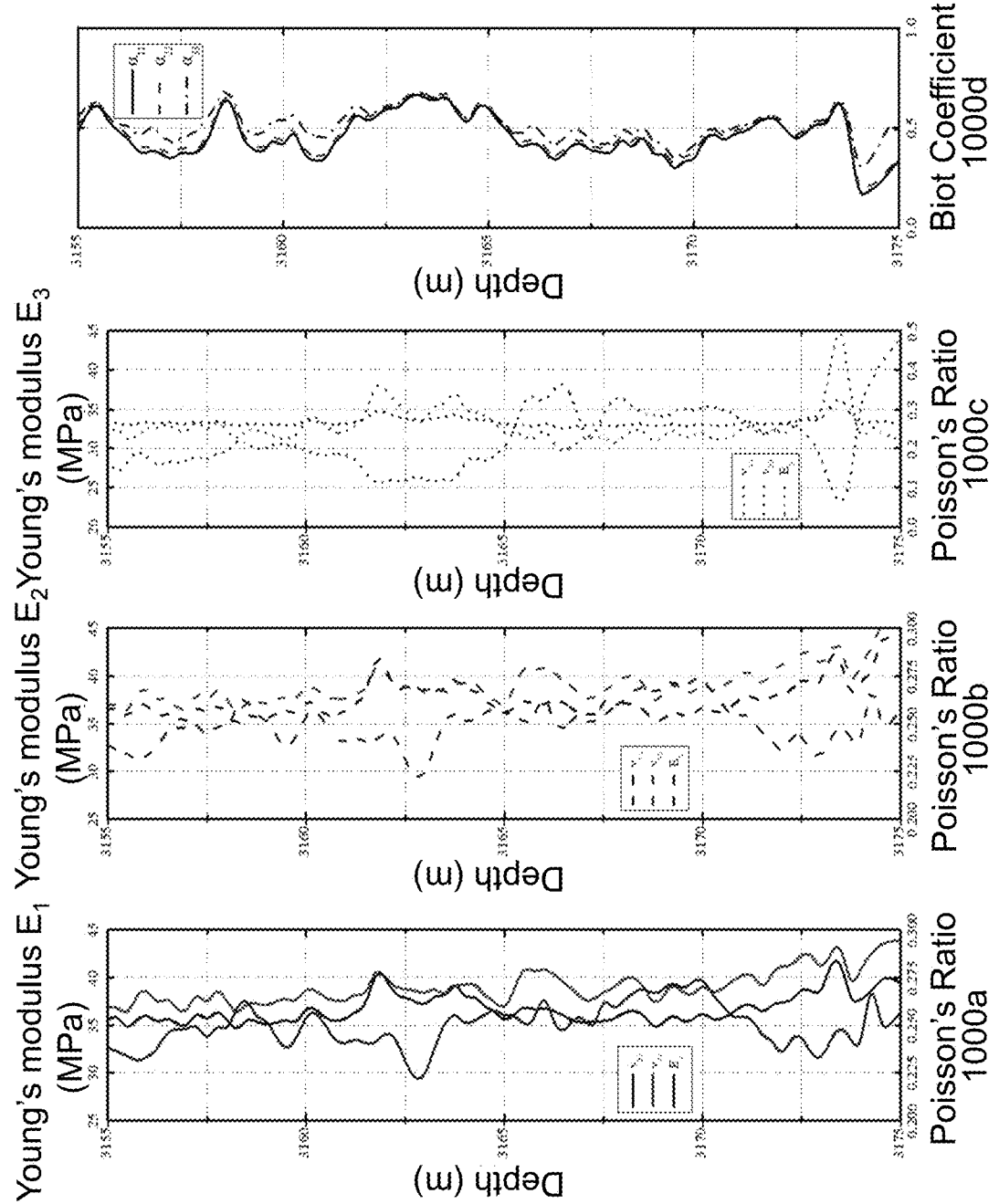
FIG. 10 illustrates static elastic parameters and an anisotropy Biot coefficient of an orthotropic rock determined based on an orthotropic rock physics model according to some embodiments of the present disclosure.

FIG. 10 illustrates static elastic parameters and an anisotropy Biot coefficient of an orthotropic rock determined based on an orthotropic rock physics model according to some embodiments of the present disclosure. One or more horizontal in-situ stresses (e.g., a maximum horizontal in-situ stress, a minimum horizontal in-situ stress) may be determined based on the static elastic parameters and the anisotropy Biot coefficient.

Figure 11:
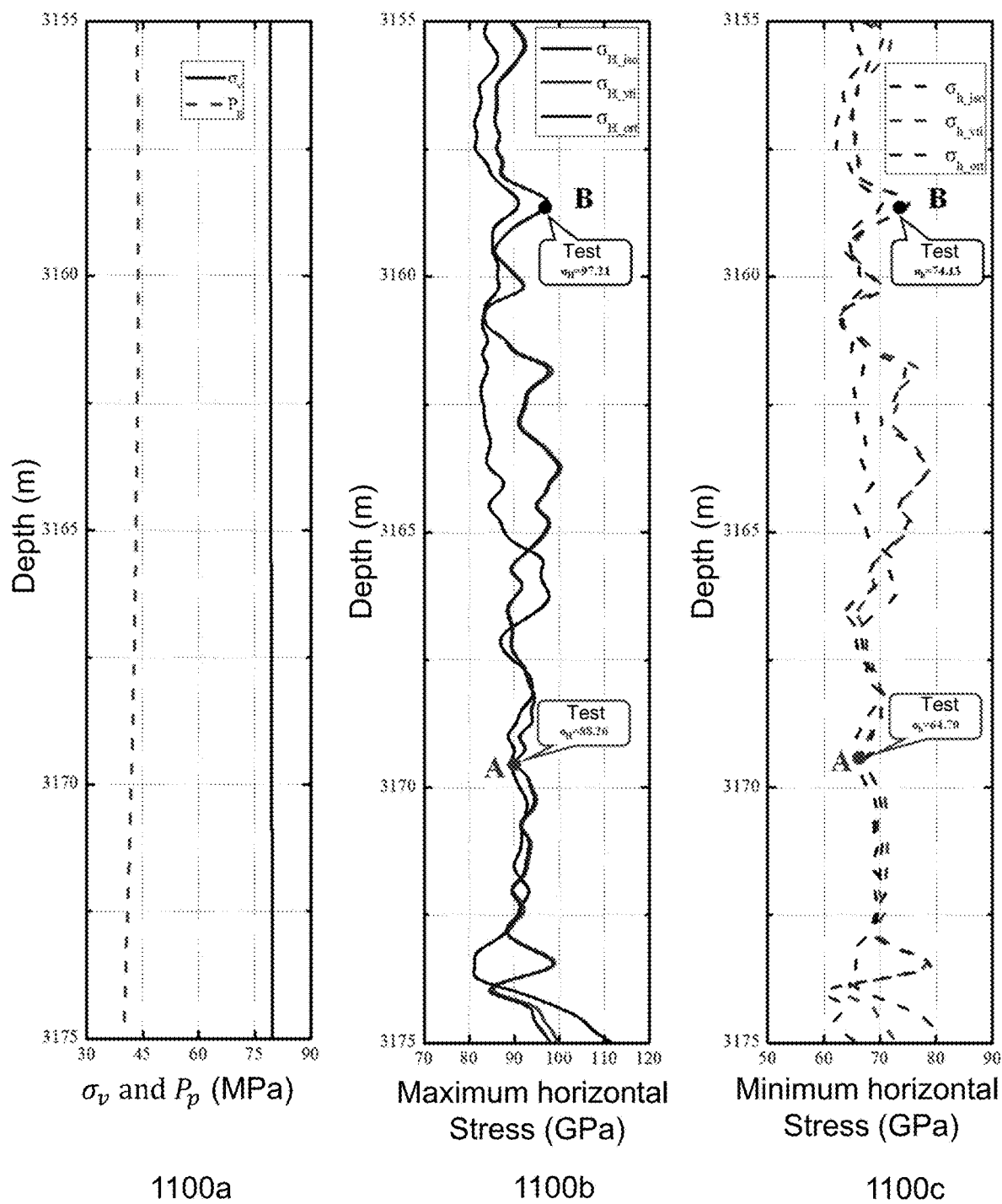
FIG. 11 illustrates a measure result of a formation pore pressure and comparing results of in-situ stresses determined based on different rock physics models according to some embodiments of the present disclosure.

FIG. 11 illustrates a measure result of a formation pore pressure and comparing results of in-situ stresses determined based on different rock physics models according to some embodiments of the present disclosure. As illustrated in FIG. 11, in Chart 1100a, $\sigma_v$ represents a vertical in-situ stress, $P_p$ represents the formation pore pressure. Chart 1100b represents maximum horizontal in-situ stresses determined based on different rock physics models. Point A of Chart 1100b represents a maximum horizontal in-situ stress calculated from a fracturing construction curve, and its value is 88.26 MPa. Point B of Chart 1100b represents a maximum horizontal in-situ stress determined by an acoustic emission experiment (based on the Kaiser effect) of a core at 3161.8 m, and its value is 95.21 MPa. At a point corresponding to the depth of point B of Chart 1100b, a prediction maximum horizontal in-situ stress of a saturated fluid ORT rock physics model is 98.98 MPa, a prediction maximum horizontal in-situ stress of a dry ORT rock physics model is 100.15 MPa, and a prediction maximum horizontal in-situ stress of a dry VTI rock physics model is 84.79 MPa. The errors (between a predicted in-situ stress and an actual result) corresponding to the three models are 3.96%, 5.19%, and 10.94% respectively. The saturated fluid ORT rock physics model has the highest accuracy and the dry VTI model has the worst accuracy.

Chart 1100c represents minimum horizontal in-situ stresses determined based on different rock physics models. Point A of Chart 1100c represents a minimum horizontal in-situ stress calculated from a fracturing construction curve, and its value is 64.70 MPa. Point B of Chart 1100c represents a minimum horizontal in-situ stress determined by an acoustic emission experiment (based on the Kaiser effect) of a core at 3161.8 m, and its value is 74.13 MPa. At a point corresponding to the depth of point B of Chart 1100c, a prediction minimum horizontal in-situ stress of a saturated fluid ORT rock physics model is 75.55 MPa, a prediction minimum horizontal in-situ stress of a dry ORT rock physics model is 78.40 MPa, and a prediction minimum horizontal in-situ stress of a dry VTI rock physics model is 68.09 MPa. The errors (between a predicted in-situ stress and an actual result) corresponding to the three models are 1.92%, 5.76%, and 8.15% respectively. The saturated fluid ORT rock physics model has the highest accuracy and the dry VTI model has the worst accuracy.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer-readable program code embodied thereon.

A non-transitory computer-readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer-readable signal medium may be any computer-readable medium that is not a computer-readable storage medium and that may communicate, propagate, or transport a program for use by or in connection with an instruction execution system, apparatus, or device. Program code embodied on a computer-readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python or the like, conventional procedural programming languages, such as the "C" programming language, Visual Basic, Fortran, Per, COBOL, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate" or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method comprising:
    acquiring, by an inductive device, measurement signals of an orthotropic rock by well logging, mud logging, or indoor testing;

collecting, by a ground recording instrument vehicle, the measurement signals from the inductive device in real time;

determining, by one or more processors, multiple physical parameters of the orthotropic rock based on the measurement signals, the multiple physical parameters including compositions of minerals, a content of each of the minerals, compositions of formation fluids, a content of each of the formation fluids, a porosity, and a saturation;

constructing, by the one or more processors, an orthotropic rock physics model based on the multiple physical parameters;

determining, by the one or more processors based on the orthotropic rock physics model, stiffness coefficients;

determining, by the one or more processors based on the following relationship formulas between stiffness coefficient and elastic parameter, multiple dynamic elastic parameters of the orthotropic rock, $$\begin{cases} E_1 = \Delta/(c_{23}^2 - c_{22}c_{33}) \\ E_2 = \Delta/(c_{13}^2 - c_{11}c_{33}) \\ E_3 = \Delta/(c_{12}^2 - c_{11}c_{22}) \end{cases}$$

$$\Delta = c_{33}c_{12}^2 + c_{22}c_{13}^2 + c_{11}c_{23}^2 - c_{11}c_{22}c_{33} - 2c_{12}c_{13}c_{23}$$

$$\begin{cases} \alpha_{11} = 1 - \dfrac{c_{11}^{dry} + c_{12}^{dry} + c_{13}^{dry}}{c_{11}^{m} + c_{12}^{m} + c_{13}^{m}} \\ \alpha_{22} = 1 - \dfrac{c_{12}^{dry} + c_{22}^{dry} + c_{23}^{dry}}{c_{11}^{m} + c_{22}^{m} + c_{23}^{m}} \\ \alpha_{33} = 1 - \dfrac{c_{13}^{dry} + c_{23}^{dry} + c_{33}^{dry}}{c_{13}^{m} + c_{23}^{m} + c_{33}^{m}} \end{cases}$$

-continued $$\begin{cases} v_{12} = (c_{13}c_{23} - c_{12}c_{33})/(c_{23}^2 - c_{22}c_{33}) \\ v_{13} = (c_{12}c_{23} - c_{13}c_{22})/(c_{23}^2 - c_{22}c_{33}) \\ v_{21} = (c_{13}c_{23} - c_{12}c_{33})/(c_{13}^2 - c_{11}c_{33}) \\ v_{23} = (c_{12}c_{13} - c_{11}c_{23})/(c_{13}^2 - c_{11}c_{33}) \\ v_{31} = (c_{12}c_{23} - c_{13}c_{22})/(c_{12}^2 - c_{11}c_{22}) \\ v_{32} = (c_{12}c_{13} - c_{11}c_{23})/(c_{12}^2 - c_{11}c_{22}) \end{cases}$$

$$\begin{cases} E_2 v_{12} = E_1 v_{21} \\ E_3 v_{13} = E_1 v_{31} \\ E_2 v_{32} = E_3 v_{23} \end{cases}$$

$$\begin{cases} \mu_{23} = c_{44} \\ \mu_{13} = c_{55} \\ \mu_{12} = c_{66} \end{cases}$$

where $C_{11}$, $C_{12}$, $C_{13}$, $c_{22}$, $C_{23}$, $c_{44}$, $c_{55}$, and $c_{66}$ denote the stiffness coefficients of the orthotropic rock, GPa; $E_1$ denotes a Young's modulus along a direction of a maximum horizontal in-situ stress, GPa; $E_2$ denotes a Young's modulus along a direction of a minimum horizontal in-situ stress, GPa; $E_3$ denotes a Young's modulus along a direction of a vertical in-situ stress, GPa; $v_{12}$ denotes a Poisson's ratio along the direction of the minimum horizontal in-situ stress and perpendicular to the direction of the maximum horizontal in-situ stress; $v_{13}$ denotes a Poisson's ratio along the direction of the vertical in-situ stress and perpendicular to the direction of the maximum horizontal in-situ stress; $v_{21}$ denotes a Poisson's ratio along the direction of the maximum horizontal in-situ stress and perpendicular to the direction of the minimum horizontal in-situ stress; $v_{23}$ a Poisson's ratio along the direction of the vertical in-situ stress and perpendicular to the direction of the minimum horizontal in-situ stress; a Poisson's ratio along the direction of the maximum horizontal in-situ stress and perpendicular to the direction of the vertical in-situ stress; and $v_{32}$ denotes a Poisson's ratio along the direction of the minimum horizontal in-situ stress and perpendicular to the direction of the vertical in-situ stress;

determining, by the one or more processors based on the multiple dynamic elastic parameters of the orthotropic rock, multiple static elastic parameters of the orthotropic rock according to relationships between the multiple dynamic elastic parameters and the multiple static elastic parameters;

determining, by the one or more processors, anisotropy Biot coefficients of the orthotropic rock physics model according to the following formulas:

where $c_{11}^{dry}$, $c_{12}^{dry}$, $c_{13}^{dry}$, $c_{22}^{dry}$, $c_{23}^{dry}$, and $c_{33}^{dry}$ denote stiffness coefficients of a dry orthotropic (ORT) rock, GPa; $c_{11}{}^m$, 2, $c_{12}{}^m$, $c_{13}{}^m$, $c_{22}{}^m$, $c_{23}{}^m$ and $c_{33}{}^m$ denote stiffness coefficients of a dry vertical transverse isotropy (VTI) rock, GPa; and $\alpha_{11}$, $\alpha_{22}$, and $\alpha_{33}$ denote the anisotropy Biot coefficients;

determining, by the one or more processors, a formation pore pressure based on longitudinal wave time differences according to an Eaton method described as the following formula:

$$P_p = \sigma_v - (\sigma_v - p_w)(AC_n/AC)^c$$

where $\sigma_v$, denotes the vertical in-situ stress, MPa; $p_w$ denotes a formation hydrostatic column pressure, MPa; $AC_n$, denotes a longitudinal wave time difference of trend line at normal pressure, μs/ft; AC denotes an actual longitudinal wave time difference, μs/ft; and $P_p$ denotes the formation pore pressure, MPa; and determining, by the one or more processors, the maximum horizontal in-situ stress and the minimum horizontal in-situ stress of the orthotropic rock according to the following formulas:

$$\begin{cases} \sigma_H = \dfrac{v_{13} + v_{12}v_{23}}{1 - v_{12}v_{21}}(\sigma_v - \alpha_{33}P_p) + \alpha_{11}P_p + \dfrac{E_1}{1 - v_{12}v_{21}}\varepsilon_H + \dfrac{E_1 v_{21}}{1 - v_{12}v_{21}}\varepsilon_h \\ \sigma_h = \dfrac{v_{23} + v_{13}v_{21}}{1 - v_{12}v_{21}}(\sigma_v - \alpha_{33}P_p) + \alpha_{22}P_p + \dfrac{E_2}{1 - v_{12}v_{21}}\varepsilon_h + \dfrac{E_1 v_{21}}{1 - v_{12}v_{21}}\varepsilon_H \end{cases}$$

where $\sigma_H$, denotes the maximum horizontal in-situ stress, MPa; $\sigma_h$ denotes the minimum horizontal in-situ stress, MPa; $\varepsilon_H$ denotes a maximum horizontal strain corresponding to the direction of the maximum horizontal in-situ stress; and $\varepsilon_h$ denotes a minimum horizontal strain corresponding to the direction of the minimum horizontal in-situ stress.

2. The method of claim 1, wherein the constructing an orthotropic rock physics model includes:

determining an equivalent elastic modulus of matrix minerals using Hashin-Shtrikman bounds;

constructing a dry matrix rock by adding inorganic pores to the matrix minerals using an isotropic self-consistent approximation (SCA) model and an isotropic differential effective medium (DEM) model to establish a dry matrix rock physics model and determine an equivalent elastic modulus of the dry matrix rock;

determining an equivalent elastic stiffness tensor of organic minerals using an anisotropic SCA model and an anisotropic DEM model;

determining an equivalent elastic stiffness tensor of an oriented organic rock based on a confidence level (CL) coefficient and the Bond transform normal distribution, wherein the CL coefficient describes a layered distribution of the organic minerals;

constructing a dry organic rock by adding organic pores to the oriented organic rock based on the anisotropic DEM model to establish a dry organic rock physics model and determine an equivalent elastic stiffness tensor of the dry organic rock;

constructing a dry vertical transverse isotropy (VTI) rock including pores by adding the dry matrix rock to the dry organic rock based on the anisotropic DEM model to establish a dry VTI rock physics model and determine an elastic tensor of the dry VTI rock;

constructing a dry orthotropic (ORT) rock by adding vertically distributed fractures to the dry VTI rock based on an anisotropy Schoenberg linear sliding model to establish a dry ORT rock physics model;

determining and converting a bulk modulus of gas-water mixture in the pores into a stiffness tensor based on a Wood formula according to a gas saturation and a water saturation; and by combining with orthotropic nature of the dry ORT rock, constructing a saturated fluid ORT rock by adding the formation fluids to the dry ORT rock based on a Brown-Korringa model to establish the orthotropic rock physics model.

3. The method of claim 2, wherein the determining an equivalent elastic modulus of matrix minerals using Hashin-Shtrikman bounds includes:

determining a maximum bulk modulus, a minimum of bulk modulus, a maximum shear modulus, and a minimum shear modulus of the matrix minerals using the Hashin-Shtrikman bounds;

designating an average of the maximum bulk modulus and the minimum bulk modulus as the bulk modulus of the matrix minerals; and designating an average of the maximum shear modulus and the minimum shear modulus as the shear modulus of the matrix minerals.

4. The method of claim 2, wherein the Hashin-Shtrikman bounds is as the following formula:

$$\begin{cases} K^{HS+} = \Lambda(\mu_{max}), K^{HS-} = \Lambda(\mu_{min}) \\ \mu^{HS+} = \Gamma(\zeta(K_{max}, \mu_{max})), \mu^{HS-} = \gamma(\zeta(K_{min}, \mu_{min})) \end{cases}$$

where $K^{HS+}$ denotes the maximum bulk modulus, GPa; $K^{HS-}$ denotes the minimum bulk modulus, GPa; $\mu^{HS+}$ denotes the maximum shear modulus, GPa; and $\mu^{HS-}$ denotes the minimum shear modulus, GPa.

5. The method of claim 2, wherein the isotropic SCA model is as the following formula:

$$\begin{cases} \sum_{i=1}^{N} v_i(K_i - K_{SCA}^+)P^{*i} = 0 \\ \sum_{i=1}^{N} v_i(\mu_i - \mu_{SCA}^+)Q^{*i} = 0 \end{cases}$$

where $v_i$ denotes a volume fraction of the i-th material; $P^{*i}$ denotes a first geometric factor of the i-th material; $Q^{*i}$ denotes a second geometric factor of the i-th material; $K_{SCA}^+$ denotes an equivalent bulk modulus, GPa; and $\mu_{SCA}^+$ denotes an equivalent shear modulus, GPa; and the isotropic DEM model is as the following formula:

$$\begin{cases} (1-v)\dfrac{d}{dv}[K^+(v)] = (K_2 - K^+)P^{(*2)}(v) \\ (1-v)\dfrac{d}{dv}[\mu^+(v)] = (\mu_2 - \mu^+)Q^{(*2)}(v) \end{cases}$$

where $K_1$ denotes a bulk modulus of a background medium, GPa; $\mu_1$ denotes a shear modulus of the background medium, GPa; $K_2$ denotes a bulk modulus of an inclusion, GPa; $\mu_2$ denotes a shear modulus of the inclusion, GPa; and $v$ denotes a volume fraction of the inclusion.

6. The method of claim 2, wherein the anisotropic SCA model is as the following formula:

$$\tilde{C}_{ijkl}^{SCA} = \sum_{n=l}^{N} v_n \tilde{C}_{ijkl}^n \left(\tilde{I}_{ijkl} + \tilde{G}_{ijkl}^n \left(\tilde{C}_{ijkl}^n - \tilde{C}_{ijkl}^{SCA}\right)\right)^{-1}$$

$$\left\{\sum_{p=l}^{N} v_p \left(\tilde{I}_{ijkl} + \tilde{G}_{ijkl}^p \left(\tilde{C}_{ijkl}^p - \tilde{C}_{ijkl}^{SCA}\right)\right)^{-1}\right\}^{-1}$$

where $\tilde{C}_{ijkl}^{SCA}$ denotes an equivalent stiffness tensor of the anisotropic SCA model, GPa; $\tilde{G}_{ijkl}^n$ denotes an Eshelby stiffness tensor of the n-th material, GPa; $\tilde{I}_{ijkl}$ denotes a fourth order unit stiffness tensor; $\tilde{C}_{ijkl}^n$ denotes a stiffness tensor of the n-th material, GPa; and $v_n$ denotes a volume fraction of the n-th material; and the anisotropic DEM model is as the following formula:

$$\frac{d}{dv}(\tilde{C}_{ijkl}^{DEM}(v)) = \frac{1}{(1-v)}(\tilde{C}_{ijkl}^{I} - \tilde{C}_{ijkl}^{DEM}(v))[\tilde{I}_{ijkl} + \tilde{G}_{ijkl}^{I}(\tilde{C}_{ijkl}^{P} - \tilde{C}_{ijkl}^{DEM}(v))]^{-1}$$

where $\tilde{C}_{ijkl}^{DBM}$ denotes a stiffness tensor of the background medium, GPa; $\tilde{C}_{ijkl}^{I}$ denotes a stiffness tensor of the inclusion, GPa; $\tilde{C}_{ijkl}^{I}$ denotes an Eshelby stiffness tensor of the inclusion; $\tilde{I}_{ijkl}$ denotes the fourth order unit stiffness tensor; and v denotes a volume fraction of a material being added, decimal.

7. The method of claim 2, wherein the anisotropy Schoenberg linear sliding model is as the following formula:

$$C = \begin{bmatrix} c_{11b} - \frac{\Delta_N c_{12b}^2}{c_{11b}} & c_{12b}(1-\Delta_N) & c_{13b}\left(1 - \frac{\Delta_N c_{12b}}{c_{11b}}\right) & 0 & 0 & 0 \\ c_{12b}(1-\Delta_N) & c_{11b}(1-\Delta_N) & c_{13b}(1-\Delta_N) & 0 & 0 & 0 \\ c_{13b}\left(1 - \frac{\Delta_N c_{12b}}{c_{11b}}\right) & c_{13b}(1-\Delta_N) & c_{33b}\left(1 - \frac{\Delta_N c_{13b}^2}{c_{11b}}\right) & 0 & 0 & 0 \\ 0 & 0 & 0 & c_{44b} & 0 & 0 \\ 0 & 0 & 0 & 0 & c_{44b}(1-\Delta_V) & 0 \\ 0 & 0 & 0 & 0 & 0 & c_{66b}(1-\Delta_H) \end{bmatrix}$$

where C denotes a stiffness matrix of the dry ORT rock after adding the vertically distributed fractures, GPa; $c_{11b}$, $c_{12}$, $c_{13b}$, $c_{33b}$, $c_{44b}$, and $c_{66b}$ denote stiffness coefficients of the dry VTI rock without the vertically distributed fractures, GPa; and $\Delta_n$, $\Delta_v$, and $\Delta_H$ denote weak degrees of characteristics of the vertically distributed fractures.

8. The method of claim 2, wherein the Wood formula is as the following formula:

$$\begin{cases} K_f = \frac{K_g K_w}{S_g K_w + (1-S_g)_{K_g}} \\ \mu_f = 0 \end{cases}$$

where $K_g$ denotes a bulk modulus of gas, GPa; $K_w$ denotes a bulk modulus of water, GPa; $K_f$ denotes an equivalent bulk modulus of the formation fluids, GPa; $S_g$ denotes a gas saturation; and $\mu_f$ denotes an equivalent shear modulus of the formation fluids, GPa; and the Brown-Korringa model is as the following formula:

$$S_{ijkl}^{sat} = S_{ijkl}^{dry} - \frac{(S_{ijmm}^{dry} - S_{ijmm}^{gr})(S_{nnkl}^{dry} - S_{nnkl}^{gr})}{(S_{aabb}^{dry} - S_{aabb}^{gr}) + \varnothing(\beta_{fl} - \beta_{gr})}$$

where $S_{ijkl}^{sat}$ denotes a flexibility tensor of the saturated fluid ORT rock, GPa$^{-1}$; $S_{ijkl}^{dry}$ denotes a flexibility tensor of the day ORT rock, GPa$^{-1}$; $S_{ijmm}^{gr}$ denotes a flexibility tensor of the dry VTI rock, GPa$^{-1}$; $\beta_{fl}$ denotes a compressibility factor of the formation fluids, GPa$^{-1}$; $\beta_{gr}$ denotes a compressibility factor of the minerals, GPa$^{-1}$; and $\varnothing$ denotes the porosity.

9. The method of claim 1, wherein the determining each of the relationships between the multiple dynamic elastic parameters and the multiple static elastic parameters includes:

determining a dynamic elastic parameter of a core of the orthotropic rock based on one or more wave speeds of the core;

determining a static elastic parameter of the core by performing a rock triaxial compression experiment on the core of the orthotropic rock; and determining the relationship between the dynamic elastic parameter and the static elastic parameter.

10. A system comprising:

an inductive device configured to acquire measurement signals of an orthotropic rock by well logging, mud logging, or indoor testing;

a ground recording instrument vehicle configured to collect the measurement signals from the inductive device in real time;

at least one storage device storing executable instructions, and at least one processor in communication with the at least one storage device, wherein when executing the executable instructions, the at least one processor is directed to cause the system to perform operations including:

obtaining the measurement signals from the one or more storage devices or the ground recording instrument vehicle;

determining multiple physical parameters of the orthotropic rock based on the measurement signals, the multiple physical parameters including compositions of minerals, a content of each of the minerals, compositions of formation fluids, a content of each of the formation fluids, a porosity, and a saturation;

constructing an orthotropic rock physics model based on the multiple physical parameters;

determining, based on the orthotropic rock physics model, stiffness coefficients;

determining, based on the following relationship formulas between stiffness coefficient and elastic parameter, multiple dynamic elastic parameters of the orthotropic rock, $$\begin{cases} E_1 = \Delta/(c_{23}^2 - c_{22}c_{33}) \\ E_2 = \Delta/(c_{13}^2 - c_{11}c_{33}) \\ E_3 = \Delta/(c_{12}^2 - c_{11}c_{22}) \end{cases}$$

$$\Delta = c_{33}c_{12}^2 + c_{22}c_{13}^2 + c_{11}c_{23}^2 - c_{11}c_{22}c_{33} - 2c_{12}c_{13}c_{23}$$

-continued $$\begin{cases} v_{12} = (c_{13}c_{23} - c_{12}c_{33})/(c_{23}^2 - c_{22}c_{33}) \\ v_{13} = (c_{12}c_{23} - c_{13}c_{22})/(c_{23}^2 - c_{22}c_{33}) \\ v_{21} = (c_{13}c_{23} - c_{12}c_{33})/(c_{13}^2 - c_{11}c_{33}) \\ v_{23} = (c_{12}c_{13} - c_{11}c_{23})/(c_{13}^2 - c_{11}c_{33}) \\ v_{31} = (c_{12}c_{23} - c_{13}c_{22})/(c_{12}^2 - c_{11}c_{22}) \\ v_{32} = (c_{12}c_{13} - c_{11}c_{23})/(c_{12}^2 - c_{11}c_{22}) \end{cases}$$

$$\begin{cases} E_2 v_{12} = E_1 v_{21} \\ E_3 v_{13} = E_1 v_{31} \\ E_2 v_{32} = E_3 v_{23} \end{cases}$$

$$\begin{cases} \mu_{23} = c_{44} \\ \mu_{13} = c_{55} \\ \mu_{12} = c_{66} \end{cases}$$

where $c_{11}$, $c_{12}$, $c_{13}$, $c_{22}$, $c_{23}$, $c_{33}$, , $c_{44}$, $c_{55}$, and $c_{66}$ denote the stiffness coefficients of the orthotropic rock, GPa; $E_1$ denotes a Young's modulus along a direction of a maximum horizontal in-situ stress, GPa; $E_2$ denotes a Young's modulus along a direction of a minimum horizontal in-situ stress, GPa; $E_3$ denotes a Young's modulus along a direction of a vertical in-situ stress, GPa; $v_{12}$ denotes a Poisson's ratio along the direction of the minimum horizontal in-situ stress and perpendicular to the direction of the maximum horizontal in-situ stress; $v_{12}$ denotes a Poisson's ratio along the direction of the vertical in-situ stress and perpendicular to the direction of the maximum horizontal in-situ stress; $v_{13}$ denotes a Poisson's ratio along the direction of the maximum horizontal in-situ stress and perpendicular to the direction of the minimum horizontal in-situ stress; $v_{23}$ a Poisson's ratio along the direction of the vertical in-situ stress and perpendicular to the direction of the minimum horizontal in-situ stress; $v_{31}$ a Poisson's ratio along the direction of the maximum horizontal in-situ stress and perpendicular to the direction of the vertical in-situ stress; and $v_{32}$ denotes a Poisson's ratio along the direction of the minimum horizontal in-situ stress and perpendicular to the direction of the vertical in-situ stress;

determining, based on the multiple dynamic elastic parameters of the orthotropic rock, multiple static elastic parameters of the orthotropic rock according to relationships between the multiple dynamic elastic parameters and the multiple static elastic parameters;

determining anisotropy Biot coefficients of the orthotropic rock physics model according to the following formulas:

$$\begin{cases} \alpha_{11} = 1 - \frac{c_{11}^{dry} + c_{12}^{dry} + c_{13}^{dry}}{c_{11}^m + c_{12}^m + c_{13}^m} \\ \alpha_{22} = 1 - \frac{c_{12}^{dry} + c_{22}^{dry} + c_{23}^{dry}}{c_{11}^m + c_{22}^m + c_{23}^m} \\ \alpha_{33} = 1 - \frac{c_{13}^{dry} + c_{23}^{dry} + c_{33}^{dry}}{c_{13}^m + c_{23}^m + c_{33}^m} \end{cases}$$

where $c_{11}^{dry}$, $c_{12}^{dry}$, $c_{13}^{dry}$, $c_{22}^{dry}$, $c_{23}^{dry}$, and $c_{33}^{dry}$ denote stiffness coefficients of a dry orthotropic (ORT) rock, GPa; $c_{11}^m$, chd $12^m$, $c_{13}^m$, $c_{22}^m$, $c_{23}$, and $c_{23}^m$ denote stiffness coefficients of a dry vertical transverse isotropy (VTI) rock, GPa; and $\alpha_{11}$, $\alpha_{22}$, and $\alpha_{33}$ denote the anisotropy Biot coefficients;

determining a formation pore pressure based on longitudinal wave time differences according to an Eaton method described as the following formula:

$$P_p = \sigma_v - (\sigma_v - p_w)(AC_n/AC)^c$$

where $\sigma_v$ denotes the vertical in-situ stress, MPa; $p_w$ denotes a formation hydrostatic column pressure, MPa; $AC_n$ denotes a longitudinal wave time difference of trend line at normal pressure, μs/ft; AC denotes an actual longitudinal wave time difference, μs/ft; and $P_p$ denotes the formation pore pressure, MPa; and determining the maximum horizontal in-situ stress and the minimum horizontal in-situ stress of the orthotropic rock according to the following formulas:

$$\begin{cases} \sigma_H = \frac{v_{13} + v_{12}v_{23}}{1 - v_{12}v_{21}}(\sigma_v - \alpha_{33}P_p) + \alpha_{11}P_p + \frac{E_1}{1 - v_{12}v_{21}}\varepsilon_H + \frac{E_1 v_{21}}{1 - v_{12}v_{21}}\varepsilon_h \\ \sigma_h = \frac{v_{23} + v_{13}v_{21}}{1 - v_{12}v_{21}}(\sigma_v - \alpha_{33}P_p) + \alpha_{22}P_p + \frac{E_2}{1 - v_{12}v_{21}}\varepsilon_h + \frac{E_1 v_{21}}{1 - v_{12}v_{21}}\varepsilon_H \end{cases}$$

where $\sigma_H$ denotes the maximum horizontal in-situ stress, MPa; $\sigma_h$ denotes the minimum horizontal in-situ stress, MPa; $\varepsilon_H$ denotes a maximum horizontal strain corresponding to the direction of the maximum horizontal in-situ stress; and $\varepsilon_h$ denotes a minimum horizontal strain corresponding to the direction of the minimum horizontal in-situ stress.

11. The system of claim 10, wherein the constructing an orthotropic rock physics model includes:

determining an equivalent elastic modulus of matrix minerals using Hashin-Shtrikman bounds;

constructing a dry matrix rock by adding inorganic pores to the matrix minerals using an isotropic self-consistent approximation (SCA) model and an isotropic differential effective medium (DEM) model to establish a dry matrix rock physics model and determine an equivalent elastic modulus of the dry matrix rock;

determining an equivalent elastic stiffness tensor of organic minerals using an anisotropic SCA model and an anisotropic DEM model;

determining an equivalent elastic stiffness tensor of an oriented organic rock based on a confidence level (CL) coefficient and the Bond transform normal distribution, wherein the CL coefficient describes a layered distribution of the organic minerals;

constructing a dry organic rock by adding organic pores to the oriented organic rock based on the anisotropic DEM model to establish a dry organic rock physics model and determine an equivalent elastic stiffness tensor of the dry organic rock;

constructing a dry vertical transverse isotropy (VTI) rock including pores by adding the dry matrix rock to the dry organic rock based on the anisotropic DEM model to establish a dry VTI rock physics model and determine an elastic tensor of the dry VTI rock;

constructing a dry orthotropic (ORT) rock by adding vertically distributed fractures to the dry VTI rock based on an anisotropy Schoenberg linear sliding model to establish a dry ORT rock physics model;

determining and converting a bulk modulus of gas-water mixture in the pores into a stiffness tensor based on a Wood formula according to a gas saturation and a water saturation; and combining with orthotropic nature of the dry ORT rock, constructing a saturated fluid ORT rock by adding the formation fluids to the dry ORT rock based on a Brown-Korringa model to establish the orthotropic rock physics model.

12. The system of claim 11, wherein the determining an equivalent elastic modulus of matrix minerals using Hashin-Shtrikman bounds includes:
   determining a maximum bulk modulus, a minimum of bulk modulus, a maximum shear modulus, and a minimum shear modulus of the matrix minerals using the Hashin- Shtrikman bounds;
   designating an average of the maximum bulk modulus and the minimum bulk modulus as the bulk modulus of the matrix minerals; and
   designating an average of the maximum shear modulus and the minimum shear modulus as the shear modulus of the matrix minerals.

13. The system of claim 11, wherein the Hashin-Shtrikman bounds is as the following formula:

$$\begin{cases} K^{HS+} = \Lambda(\mu_{max}), K^{HS-} = \Lambda(\mu_{min}) \\ \mu^{HS+} = \Gamma(\zeta(K_{max}, \mu_{max})), \mu^{HS-} = \gamma(\zeta(K_{min}, \mu_{min})) \end{cases}$$

where $K^{HS+}$ denotes the maximum bulk modulus, GPa; $K^{HS-}$ denotes the minimum bulk modulus, GPa; $\mu^{HS+}$ denotes the maximum shear modulus, GPa; and $\mu^{HS-}$ denotes the minimum shear modulus, GPa.

14. The system of claim 11, wherein the isotropic SCA model is as the following formula:

$$\begin{cases} \sum_{i=1}^{N} v_i(K_i - K_{SCA}^+)P^{+i} = 0 \\ \sum_{i=1}^{N} v_i(\mu_i - \mu_{SCA}^+)Q^{+i} = 0 \end{cases}$$

where $v_i$ denotes a volume fraction of the i-th material; $P^{+i}$ denotes a first geometric factor of the i-th material; $Q^{+i}$ denotes a second geometric factor of the i-th material; $K_{SCA}^+$ denotes an equivalent bulk modulus, GPa; and $\mu_{SCA}^+$ denotes an equivalent shear modulus, GPa; and the isotropic DEM model is as the following formula:

$$\begin{cases} (1-v)\frac{d}{dv}[K^+(v)] = (K_2 - K^+)P^{(+2)}(v) \\ (1-v)\frac{d}{dv}[\mu^+(v)] = (\mu_2 - \mu^+)Q^{(+2)}(v) \end{cases}$$

where $K_1$ denotes a bulk modulus of a background medium, GPa; $\mu_1$ denotes a shear modulus of the background medium, GPa; $K_2$ denotes a bulk modulus of an inclusion, GPa; $\mu_2$, denotes a shear modulus of the inclusion, GPa; and v denotes a volume fraction of the inclusion.

15. The system of claim 11, wherein the anisotropic SCA model is as the following formula:

$$\tilde{C}_{ijkl}^{SCA} = \sum_{i=1}^{N} v_n \tilde{C}_{ijkl}^n (\tilde{I}_{ijkl} + \tilde{G}_{ijkl}^n (\tilde{C}_{ijkl}^n - \tilde{C}_{ijkl}^{SCA}))^{-1}$$

$$\left\{ \sum_{p=l}^{N} v_p (\tilde{I}_{ijkl} + \tilde{G}_{ijkl}^p (\tilde{C}_{ijkl}^p - \tilde{C}_{ijkl}^{SCA}))^{-1} \right\}^{-1}$$

where $\tilde{C}_{ijkl}^{SCA}$ denotes an equivalent stiffness tensor of the anisotropic SCA model, GPa; $\tilde{G}_{ijkl}^n$ denotes an Eshelby stiffness tensor of the n-th material, GPa; $\tilde{I}_{ijkl}$ denotes a fourth order unit stiffness tensor; $\tilde{C}_{ijkl}^n$ denotes a stiffness tensor of the n-th material, GPa; and $v_n$ denotes a volume fraction of the n-th material; and the anisotropic DEM model is as the following formula:

$$\frac{d}{dv}(\tilde{C}_{ijkl}^{DEM}(v)) = \frac{1}{(1-v)}(\tilde{C}_{ijkl}^I - \tilde{C}_{ijkl}^{DEM}(v))[\tilde{I}_{ijkl} + \tilde{G}_{ijkl}^I(\tilde{C}_{ijkl}^P - \tilde{C}_{ijkl}^{DEM}(v))]^{-1}$$

where $\tilde{C}_{ijkl}^{DEM}$ denotes a stiffness tensor of the background medium, GPa; $\tilde{C}_{ijkl}^I$ denotes a stiffness tensor of the inclusion, GPa; $\tilde{C}_{ijkl}^I$ denotes an Eshelby stiffness tensor of the inclusion; $\tilde{I}_{ijkl}$ denotes the fourth order unit stiffness tensor; and v denotes a volume fraction of a material being added, decimal.

16. The system of claim 11, wherein the anisotropy Schoenberg linear sliding model is as the following formula:

$$C = \begin{bmatrix} c_{11b} - \frac{\Delta_N c_{12b}^2}{c_{11b}} & c_{12b}(1-\Delta_N) & c_{13b}\left(1 - \frac{\Delta_N c_{12b}}{c_{11b}}\right) & 0 & 0 & 0 \\ c_{12b}(1-\Delta_N) & c_{11b}(1-\Delta_N) & c_{13b}(1-\Delta_N) & 0 & 0 & 0 \\ c_{13b}\left(1 - \frac{\Delta_N c_{12b}}{c_{11b}}\right) & c_{13b}(1-\Delta_N) & c_{33b}\left(1 - \frac{\Delta_N c_{13b}^2}{c_{11b}}\right) & 0 & 0 & 0 \\ 0 & 0 & 0 & c_{44b} & 0 & 0 \\ 0 & 0 & 0 & 0 & c_{44b}(1-\Delta_V) & 0 \\ 0 & 0 & 0 & 0 & 0 & c_{66b}(1-\Delta_H) \end{bmatrix}$$

where C denotes a stiffness matrix of the dry ORT rock after adding the vertically distributed fractures, GPa; $c_{11b}$, $c_{12b}$, $c_{13b}$, $c_{33b}$, $c_{44b}$, and $c_{66b}$ denote stiffness coefficients of the dry VTI rock without the vertically distributed fractures, GPa; and $\Delta_N$, $\Delta_v$, and $\Delta_H$ denote weak degrees of characteristics of the vertically distributed fractures.

17. The system of claim 11, wherein the Wood formula is as the following formula:

$$\begin{cases} K_f = \dfrac{K_g K_w}{S_g K_w + (1-S_g)_{K_g}} \\ \mu_f = 0 \end{cases}$$

where $K_g$ denotes a bulk modulus of gas, GPa; $K_w$ denotes a bulk modulus of water, GPa; $K_f$ denotes an equivalent bulk modulus of the formation fluids, GPa; $S_g$ denotes a gas saturation; and $\mu_f$ denotes an equivalent shear modulus of the formation fluids, GPa; and the Brown-Korringa model is as the following formula:

$$S_{ijkl}^{sat} = S_{ijkl}^{dry} - \dfrac{(S_{ijmm}^{dry} - S_{ijmm}^{gr})(S_{nnkl}^{dry} - S_{nnkl}^{gr})}{(S_{aabb}^{dry} - S_{aabb}^{gr}) + \varnothing(\beta_{fl} - \beta_{gr})}$$

where $S_{ijkl}^{sat}$ denotes a flexibility tensor of the saturated fluid ORT rock, GPa$^{-1}$; $S_{ijkl}^{dry}$ denotes a flexibility tensor of the day ORT rock, GPa$^{-1}$; $S_{ijmm}^{gr}$ denotes a flexibility tensor of the dry VTI rock, GPa$^{-1}$; $\beta_{fl}$ denotes a compressibility factor of the formation fluids, GPa$^{-1}$; $\beta_{gr}$ denotes a compressibility factor of the minerals, GPa$^{-1}$; and $\varnothing$ denotes the porosity.

18. The system of claim 10, wherein the determining each of the relationships between the multiple dynamic elastic parameters and the multiple static elastic parameters includes:
   determining a dynamic elastic parameter of a core of the orthotropic rock based on one or more wave speeds of the core;
   determining a static elastic parameter of the core by performing a rock triaxial compression experiment on the core of the orthotropic rock; and
   determining the relationship between the dynamic elastic parameter and the static elastic parameter.

19. A non-transitory computer readable medium, comprising executable instructions that, when executed by at least one processor, direct the at least one processor to perform a method, the method comprising:
   causing an inductive device to acquire measurement signals of an orthotropic rock by well logging, mud logging, or indoor testing;
   causing a ground recording instrument vehicle to collect the measurement signals from the inductive device in real time;
   obtaining the measurement signals of the orthotropic rock from the ground recording instrument vehicle;
   determining multiple physical parameters of the orthotropic rock based on the measurement signals, the multiple physical parameters including compositions of minerals, a content of each of the minerals, compositions of formation fluids, a content of each of the formation fluids, a porosity, and a saturation;
   constructing an orthotropic rock physics model based on the multiple physical parameters;
   determining, based on the orthotropic rock physics model, stiffness coefficients;
   determining, based on the following relationship formulas between stiffness coefficient and elastic parameter, multiple dynamic elastic parameters of the orthotropic rock, $$\begin{cases} E_1 = \Delta/(c_{23}^2 - c_{22}c_{33}) \\ E_2 = \Delta/(c_{13}^2 - c_{11}c_{33}) \\ E_3 = \Delta/(c_{12}^2 - c_{11}c_{22}) \end{cases}$$

$$\Delta = c_{33}c_{12}^2 + c_{22}c_{13}^2 + c_{11}c_{23}^2 - c_{11}c_{22}c_{33} - 2c_{12}c_{13}c_{23}$$

$$\begin{cases} v_{12} = (c_{13}c_{23} - c_{12}c_{33})/(c_{23}^2 - c_{22}c_{33}) \\ v_{13} = (c_{12}c_{23} - c_{13}c_{22})/(c_{23}^2 - c_{22}c_{33}) \\ v_{21} = (c_{13}c_{23} - c_{12}c_{33})/(c_{13}^2 - c_{11}c_{33}) \\ v_{23} = (c_{12}c_{13} - c_{11}c_{23})/(c_{13}^2 - c_{11}c_{33}) \\ v_{31} = (c_{12}c_{23} - c_{13}c_{22})/(c_{12}^2 - c_{11}c_{22}) \\ v_{32} = (c_{12}c_{13} - c_{11}c_{23})/(c_{12}^2 - c_{11}c_{22}) \end{cases}$$

$$\begin{cases} E_2 v_{12} = E_1 v_{21} \\ E_3 v_{13} = E_1 v_{31} \\ E_2 v_{32} = E_3 v_{23} \end{cases}$$

$$\begin{cases} \mu_{23} = c_{44} \\ \mu_{13} = c_{55} \\ \mu_{12} = c_{66} \end{cases}$$

where $c_{11}$, $c_{12}$, $C_{13}$, $C_{22}$, $C_{23}$, $C_{33}$, $C_{44}$, $c_{55}$, and $c_{66}$ denote the stiffness coefficients of the orthotropic rock, GPa; $E_1$ denotes a Young's modulus along a direction of a maximum horizontal in-situ stress, GPa; $E_2$ denotes a Young's modulus along a direction of a minimum horizontal in-situ stress, GPa; $E_3$ denotes a Young's modulus along a direction of a vertical in-situ stress, GPa; $v_{12}$ denotes a Poisson's ratio along the direction of the minimum horizontal in-situ stress and perpendicular to the direction of the maximum horizontal in-situ stress; $v_{13}$ denotes a Poisson's ratio along the direction of the vertical in-situ stress and perpendicular to the direction of the maximum horizontal in-situ stress; $v_{21}$ denotes a Poisson's ratio along the direction of the maximum horizontal in-situ stress and perpendicular to the direction of the minimum horizontal in-situ stress; $v_{23}$ a Poisson's ratio along the direction of the vertical in-situ stress and perpendicular to the direction of the minimum horizontal in-situ stress; $v_{31}$ a Poisson's ratio along the direction of the maximum horizontal in-situ stress and perpendicular to the direction of the vertical in-situ stress; and $v_{32}$ denotes a Poisson's ratio along the direction of the minimum horizontal in-situ stress and perpendicular to the direction of the vertical in-situ stress;

determining, based on the multiple dynamic elastic parameters of the orthotropic rock, multiple static elastic parameters of the orthotropic rock according to relationships between the multiple dynamic elastic parameters and the multiple static elastic parameters;

determining anisotropy Biot coefficients of the orthotropic rock physics model according to the following formulas:

$$\begin{cases} \alpha_{11} = 1 - \dfrac{c_{11}^{dry} + c_{12}^{dry} + c_{13}^{dry}}{c_{11}^{m} + c_{12}^{m} + c_{13}^{m}} \\ \alpha_{22} = 1 - \dfrac{c_{12}^{dry} + c_{22}^{dry} + c_{23}^{23}}{c_{11}^{m} + c_{22}^{m} + c_{23}^{m}} \\ \alpha_{33} = 1 - \dfrac{c_{13}^{dry} + c_{23}^{dry} + c_{33}^{dry}}{c_{13}^{m} + c_{23}^{m} + c_{33}^{m}} \end{cases}$$

where $c_{11}^{dry}$, $c_{12}^{dry}$, $c_{13}^{dry}$, $c_{22}^{dry}$, $c_{23}^{dry}$, and $c_{33}^{dry}$ denote stiffness coefficients of a dry orthotropic (ORT) rock, GPa; $c_{11}^{m}$, $c_{12}^{m}$, $c_{13}^{m}$, $c_{22}^{m}$, $c_{23}^{m}$, and $c_{33hu\ m}$ denote stiffness coefficients of a dry vertical transverse isotropy (VTI) rock, GPa; and $\alpha_{11}$, $\alpha_{22}$, and $\alpha_{33}$ denote the anisotropy Biot coefficients;

determining a formation pore pressure based on longitudinal wave time differences according to an Eaton method described as the following formula:

$$P_p = \sigma_v - (\sigma_v - p_w)(AC_n/AC)^c$$

where $\sigma_v$ denotes the vertical in-situ stress, MPa; $p_w$ denotes a formation hydrostatic column pressure, MPa; $AC_n$ denotes a longitudinal wave time difference of trend line at normal pressure, μs/ft; AC denotes an actual longitudinal wave time difference, μs/ft; and $P_p$ denotes the formation pore pressure, MPa; and determining the maximum horizontal in-situ stress and the minimum horizontal in-situ stress of the orthotropic rock according to the following formulas:

$$\begin{cases} \sigma_H = \dfrac{v_{13} + v_{12}v_{23}}{1 - v_{12}v_{21}}(\sigma_v - \alpha_{33}P_p) + \alpha_{11}P_p + \dfrac{E_1}{1 - v_{12}v_{21}}\varepsilon_H + \dfrac{E_1 v_{21}}{1 - v_{12}v_{21}}\varepsilon_h \\ \sigma_h = \dfrac{v_{23} + v_{13}v_{21}}{1 - v_{12}v_{21}}(\sigma_v - \alpha_{33}P_p) + \alpha_{22}P_p + \dfrac{E_2}{1 - v_{12}v_{21}}\varepsilon_h + \dfrac{E_1 v_{21}}{1 - v_{12}v_{21}}\varepsilon_H \end{cases}$$

where $\sigma_H$ denotes the maximum horizontal in-situ stress, MPa; $\sigma_h$ denotes the minimum horizontal in-situ stress, MPa; $\varepsilon_H$ denotes a maximum horizontal strain corresponding to the direction of the maximum horizontal in-situ stress; and $\varepsilon_h$ denotes a minimum horizontal strain corresponding to the direction of the minimum horizontal in-situ stress.

20. The non-transitory computer readable medium of claim 19, wherein the constructing an orthotropic rock physics model includes:

determining an equivalent elastic modulus of matrix minerals using Hashin-Shtrikman bounds;

constructing a dry matrix rock by adding inorganic pores to the matrix minerals using an isotropic self-consistent approximation (SCA) model and an isotropic differential effective medium (DEM) model to establish a dry matrix rock physics model and determine an equivalent elastic modulus of the dry matrix rock;

determining an equivalent elastic stiffness tensor of organic minerals using an anisotropic SCA model and an anisotropic DEM model;

determining an equivalent elastic stiffness tensor of an oriented organic rock based on a confidence level (CL) coefficient and the Bond transform normal distribution, wherein the CL coefficient describes a layered distribution of the organic minerals;

constructing a dry organic rock by adding organic pores to the oriented organic rock based on the anisotropic DEM model to establish a dry organic rock physics model and determine an equivalent elastic stiffness tensor of the dry organic rock;

constructing a dry vertical transverse isotropy (VTI) rock including pores by adding the dry matrix rock to the dry organic rock based on the anisotropic DEM model to establish a dry VTI rock physics model and determine an elastic tensor of the dry VTI rock;

constructing a dry orthotropic (ORT) rock by adding vertically distributed fractures to the dry VTI rock based on an anisotropy Schoenberg linear sliding model to establish a dry ORT rock physics model;

determining and converting a bulk modulus of gas-water mixture in the pores into a stiffness tensor based on a Wood formula according to a gas saturation and a water saturation; and combining with orthotropic nature of the dry ORT rock, constructing a saturated fluid ORT rock by adding the formation fluids to the dry ORT rock based on a Brown-Korringa model to establish the orthotropic rock physics model.

* * * * *